United States Patent [19]

Gluchowski

[11] Patent Number: 5,091,528
[45] Date of Patent: Feb. 25, 1992

[54] 6- OR 7-(2-IMINO-2-IMIDAZOLIDINE)-1,4-BENZOXAZINES AS α ADRENERGIC AGENTS

[75] Inventor: Charles Gluchowski, Mission Viejo, Calif.

[73] Assignee: Allergan, Inc., Irvine, Calif.

[21] Appl. No.: 582,034

[22] Filed: Sep. 12, 1990

[51] Int. Cl.[5] .......................................... C07D 265/34
[52] U.S. Cl. .................................................... 544/105
[58] Field of Search ........................................ 544/105

[56] References Cited

U.S. PATENT DOCUMENTS

| 3,636,219 | 1/1972 | Culik et al. | 424/265 |
| 3,890,319 | 6/1975 | Danielewicz et al. | 260/250 |
| 4,515,800 | 5/1985 | Cavero et al. | 514/392 |
| 4,587,257 | 5/1986 | DeSantis et al. | 514/392 |

OTHER PUBLICATIONS

"Heteroaromatic Analogues of the α2-Adrenoreceptor Partial Agonist Clonidine", *J. Med. Chem.*, 1989, 32, 1627–1630, Chapelo et al.

Primary Examiner—Mary C. Lee
Assistant Examiner—Joseph K. McKane
Attorney, Agent, or Firm—Gabor L. Szekeres; Martin A. Voet; Robert J. Baran

[57] ABSTRACT

Compounds having α adrenergic activity and useful for the treatment of glaucoma, renal and gastrointestinal disorders and vasoconstictors have the formula

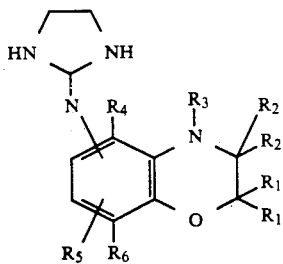

where $R_1$ is independently H, or lower alkyl or 1 to 6 carbons; $R_2$ is independently H, or lower alkyl of 1 to 6 carbons or the two $R_2$ symbols jointly represent a carbonyl oxygen; $R_3$ is H, lower alkyl of one to 6 carbons, O, OH and $OR_7$ where $R_7$ is lower alkyl of 1 to 6 carbons, or $R_3$ is COH or $COR_8$ where $R_8$ is lower alkyl of 1 to 6 carbons; $R_4$ and $R_5$ independently is H, Br, Cl, or lower alkyl of 1 to 6 carbons, lower alkenyl or lower alkynyl with the proviso that when the $R_2$ groups symbolize a carbonyl oxygen then $R_4$ and $R_5$ both cannot be hydrogen; $R_6$ is hydrogen, Br, Cl, or lower alkyl of 1 to 6 carbons, lower alkenyl or lower alkynyl, and the $R_5$ and the (2-imidazoline-2-yl)amino substituents are connected mutually exclusively to the 6 and 7 positions of the 1,4-benzoxazine nucleus.

31 Claims, No Drawings

6- OR 7-(2-IMINO-2-IMIDAZOLIDINE)-1,4-BENZOXAZINES AS α ADRENERGIC AGENTS

BACKGROUND OF THE INVENTION

1. Field of the Invention

The present invention is directed to novel 6- or 7-(2-imino-2-imidazolidine)-1,4-benzoxazines which are active as alpha adrenergic agents, and particularly which are useful for treatment of glaucoma, renal and gastrointestinal disorders, vasoconstrictors and other diseases and conditions mediated by alpha-1 and alpha-2 receptors. In another aspect, the present invention is directed to pharmaceutical formulations or compositions which incorporate the novel compounds of the invention. In still another aspect, the present invention is directed to administering such formulations and compositions for the purpose of reducing or maintaining intraocular pressure (anti-glaucoma) and as vasoconstrictors, for example for controlling ocular bleeding, in mammalian species, including humans.

2. Brief Description of the Prior Art

Alpha adrenergic agents are known in the art. Whereas alpha-1 agonists are known to include compounds which have vasoconstrictor activity and are thus useful for controlling intraocular bleeding, alpha-2 agonist are known to include compounds useful for reducing intraocular pressure (anti-glaucoma effect), for increasing renal flow (diuretics) and for altering the rate of fluid transport in the gastrointestinal tract (anti-diarrheals).

In an article titled "Heteroaromatic Analogues of the alpha$_2$-Adrenoreceptor Partial Agonist Clonidine" *J. Med. Chem.* 1989, 32, 1627–1630, Chapleo et al. describe 6-(2-iminoimidazolidine)-3-oxo-3,4-dihydro-(2H)-1,4-benzoxazine and 7-(2-imino-imidazlidine)-3-oxo-3,4-dihydro-(2H)-1,4-benzoxazi compounds as partial alpha-2 agonists.

U.S. Pat. No. 3,890,319 discloses (2-imidazolin-2-ylamino- substituted quinoxalines as regulators of the cardiovascular system.

U.S. Pat. No. 4,515,800, describes 2-(trisubstituted phenylimino)imidazoline compounds [also known as 2-(trisubstituted-anilino)-1,3-diazacyclopentene-(2) compounds] in pharmaceutical compositions, preferably in eye drops, for the treatment of glaucoma.

U.S. Pat. No. 4,587,257 discloses 2-(trisubstituted phenylimino)imidazoline compounds capable of controlling ocular bleeding;

U.S. Pat. No. 3,636,219 discloses 2-(substituted-phenylamino)-thiazolines and imidazolines having anti-cholinergic activity.

SUMMARY OF THE INVENTION

This invention covers compounds of Formula 1 where

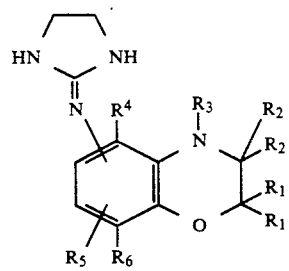

FORMULA 1 where:
$R_1$ is independently H, or lower alkyl of 1 to 6 carbons, $R_2$ is independently H, or lower alkyl of 1 to 6 carbons or the two $R_2$ symbols jointly represent a carbonyl oxygen;

$R_3$ is H, lower alkyl of one to 6 carbons, O, OH and $OR_7$ where $R_7$ is lower alkyl of 1 to 6 carbons, or $R_3$ is COH or $COR_8$ where $R_8$ is lower alkyl of 1 to 6 carbons;

$R_4$ and $R_5$ independently is H, Br, Cl, or lower alkyl of 1 to 6 carbons, lower alkenyl or lower alkynyl with the proviso that when the $R_2$ groups symbolize a carbonyl oxygen $O_2$ H then $R_4$ and $R_5$ both cannot be hydrogen;

$R_6$ is hydrogen, Br, Cl, or lower alkyl of 1 to 6 carbons, lower alkenyl or lower alkynyl, and the $R_5$ and the (2-imidazoline-2-yl)amino substituents are connected mutually exclusively to the 6 and 7 positions of the 1,4-benzoxazine nucleus.

In a second aspect, the present invention relates to the use of the compounds of Formula 1 for reducing or maintaining the intraocular pressure in a mammalian eye by administering directly to the mammalian eye a pharmaceutical composition containing an effective amount of one or more compounds of Formula 1. The compounds of Formula 1, or more precisely pharmaceutical compositions containing one or more of such compounds, are particularly useful for treating mammalian, for example human, eyes affected with glaucoma. In this regard the present invention also relates to pharmaceutical formulations comprising one or more compounds of Formula 1 admixed with a pharmaceutically acceptable excipient or carrier.

In a third aspect, the present invention also relates to the use of one or more compounds of Formula 1 admixed with suitable pharmaceutically acceptable excipients or carriers, as vasoconstrictors in a mammalian (for example human) species, and particularly as agents for controlling intraocular bleeding.

In still further aspects, the present invention relates to the use of one or more compounds of Formula 1 admixed with suitable pharmaceutically acceptable excipients or carriers, as agents for increasing renal flow (diuretics) and as agents for controlling secretion of fluids in the gastro-intestinal tract (anti-diarrhea agents).

As is known in the field, some of the above-noted therapeutic effects are attributed to alpha 1 adrenergic type biological activity, whereas other ones of the above-noted effects are attributed to alpha 2 type of biological activity. Some of the compounds of the present invention have both alpha 1 and alpha 2 type biological activity and some others are selectively alpha 2 type agents.

GENERAL EMBODIMENTS

Definitions

The terms "ester" and "amide" as used here refer to and cover any compound falling within the definition of those terms as classically used in organic chemistry.

The term "alkyl" as used here refers to and includes normal and branch chained alkyl groups as well as cyclo-alkyl groups. The term "lower alkyl", unless specifically stated otherwise, includes normal alkyl of 1 to 6 carbons, branch chained alkyl of 3 to 6 carbons and cyclo-groups having 3 to 6 carbon atoms. Similarly, the terms "alkenyl" and "alkynyl" include normal and branch chained as well as cyclo- alkenyl and alkynyl groups, respectively, having 2 to 6 carbons when the chains are normal, and 3 to 6 carbons when the chains are branched or cyclic.

A pharmaceutically acceptable salt may be prepared for any compound of this invention having a functionality capable of forming such salt, for example an acid or an amine functionality. A pharmaceutically acceptable salt may be any salt which retains the activity of the parent compound and does not impart any deleterious or untoward effect on the subject to which it is administered and in the context in which it is administered.

Such a salt may be derived from any organic or inorganic acid or base. The salt may be a mono or polyvalent ion. Of particular interest where the acid function is concerned are the inorganic ions, sodium, potassium, calcium, and magnesium. Organic amine salts may be made with amines, particularly ammonium salts such as mono-, di- and trialkyl amines or ethanol amines. Salts may also be formed with caffeine, tromethamine and similar molecules. Where there is a nitrogen sufficiently basic as to be capable of forming acid addition salts, such may be formed with any inorganic or organic acids or alkylating agent such as methyl iodide. Preferred salts are those formed with inorganic acids such as hydrochloric acid, sulfuric acid or phosphoric acid. Any of a number of simple organic acids such as mono-, di- or tri-acid may also be used.

The preferred compounds of this invention, with reference to Formula 1, and with reference to the substituents in the 2-position of the 1,4-benzoxazine nucleus ($R_1$) are those where $R_1$ is hydrogen. (Conventional numbering of the positions in the 1,4-benzoxazine nucleus is illustrated for the sake of clarity of this description in Formula 2.)

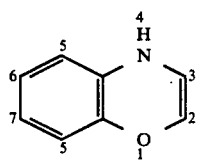

Formula 2

With reference to the substituents in the 3 position of the 1,4-benzoxazine nucleus ($R_2$), in the preferred compounds of the present invention $R_2$ is either hydrogen, or the two $R_2$ groups jointly represent an oxo function. In other words, the preferred compounds of the invention either are 2,3-dihydro-1,4-benzoxazines unsubstituted in the 2, and 3 positions, or are 2,3-dihydro-3-oxo-1,4-benzoxazines unsubstituted in the 2 position.

With respect to the N-substituent ($R_3$) in the 4 position of the 1,4-benzoxazines of the present invention, $R_3$ is preferably H, or lower alkyl of 1 to 6 carbons; even more preferably $R_3$ is H or $CH_3$.

The substituent ($R_4$) in the 5 position of the 1,4-benzoxazines of the present invention is preferably hydrogen, bromine or lower alkyl or alkenyl group; among the lower alkyl and alkenyl groups those having 1 to 3 carbons (such as methyl, ethyl, n-propyl, 2-propyl and allyl) are preferred.

With respect to the 6 and 7 positions of the benzoxazine nucleus of the compounds of the present invention, one of these positions is substituted with a 2-imino-2-imidazolidine group, as is shown in the structural Formula 1, and the other is preferably substituted with hydrogen, bromine or lower alkyl of 1 to 3 carbons, or lower alkenyl of 3 carbons.

The 8 position of the 1,4-benzoxazine nucleus of the compounds of the present invention is preferably substituted with hydrogen, bromine, lower alkyl group of 1 to 3 carbons, or lower alkenyl group of 3 carbons (allyl group).

Still more particularly preferred are compounds of the invention where, with reference to Formula 1, the 6 or 7 position bears the 2-imino-2-imidazolidine substituent, the carbon in the 3 position is unsubstituted or is oxo substituted, the nitrogen in the 4-position is either methyl substituted or is unsubstituted, and where the molecule has no further substituent in the 5, 6, 7 and 8 positions of the 1,4-benzoxazine nucleus.

Alternatively, particularly preferred are compounds of the invention where, with reference to Formula 1, the 6 or 7 position bears the 2-imino-2-imidazolidine substituent, the carbon in the 3 position is unsubstituted or is oxo substituted, the nitrogen in the 4-position is either methyl substituted or is unsubstituted, and where the 5, 6, 7 and 8 positions of the 1,4-benzoxazine nucleus jointly have a total of 1 to 3 substituents, in the form of bromo, lower alkyl group of 1 to 3 carbons, or lower alkenyl group of 3 carbons. In this regard, mono-bromo compounds where the bromine is in the 5, 6, 7 or 8 position, dibromo compounds where the bromines are in the 5 and 6, in the 5 and 7 or in the 6 and 8 positions, are preferred. Similarly, mono lower C-alkyl or lower C-alkenyl compounds are also preferred, where the alkyl or alkenyl group is either in the 5, 6, 7 or 8 position. Among the C-dialkyl or C-dialkenyl compounds those are preferred where the alkyl or alkenyl groups are in the 5 to 7 positions.

For maintaining intraocular pressure in a mammalian eye, and particularly for reducing such pressure as for treatment of glaucoma in humans suffering from that condition, the compounds of the present invention (or mixtures or salts thereof) are administered to the eye admixed with an ophtalmically acceptable carrier. Any suitable, e.g., conventional, ophtalmically acceptable carrier may be employed. A carrier is ophtalmically acceptable if it has substantially no long term or permanent detrimental effect on the eye to which it is administered. Examples of ophtalmically acceptable carriers include water (distilled or deionized water) saline and other aqueous media. The compounds of the invention are preferably soluble in the carrier which is employed for their administration, so that the compounds are administered to the eye in the form of a solution. Alternatively, a suspension of the active compound or compounds (or salts thereof) in a suitable carrier may also be employed.

The compounds of the invention (or mixtures or salts thereof) are administered in an ophtalmically acceptable carrier in sufficient concentration so as to deliver an effective amount of the active compound or compounds to the eye. Preferably, the ophtalmic, therapeutic solutions contain one or more compounds of the invention in a concentration range of approximately 0.0001% to approximately 1% (weight per volume) and more preferably approximately 0.05% to approximately 0.5% (weight per volume).

Any method of administering drugs directly to a mammalian eye may be employed to provide the presently useful compound or comounds to the eye to be treated. By the term "administering directly" is meant to exclude those general systemic drug administration modes, e.g., injection directly into the patient's blood vessels, oral administration and the like, which result in the compound or compounds being systemically available. The primary effect on the mammal resulting from the direct administering of the presently useful compound or compounds to the mammal's eye is preferably a reduction in intraocular pressure. More preferably, the presently useful compound or compounds are applied topically to the eye or are injected directly into the eye. Particularly useful results are obtained when the compound or compounds are applied topically to the eye.

Topical ophthalmic preparations, for example ocular drops, gels or creams, are preferred because of ease of application, ease of dose delivery, and fewer systemic side effects, such as cardiovascular hypotension. An exemplary topical ophthalmic formulation is shown below in Table I. The abbreviation q.s. means a quantity sufficient to effect the result or to make volume.

TABLE I

| Ingredient | Amount (% W/V) |
| --- | --- |
| Compound of the invention, for example the compound of Example 31 | about 0.0001 to about 1.0 |
| Preservative | 0–0.10 |
| Vehicle | 0–40 |
| Tonicity Adjustor | 1–10 |
| Buffer | 0.01–10 |
| pH Adjustor | q.s. pH 4.5–7.5 |
| antioxidant | as needed |
| Purified Water | as needed to make 100% |

Various preservatives may be used in the ophthalmic preparation described in Table I above. Preferred preservatives include, but are not limited to, benzalkonium chloride, chlorobutanol, thimerosal, phenylmercuric acetate, and phenylmercuric nitrate. Likewise, various preferred vehicles may be used in such ophthalmic preparation. These vehicles include, but are not limited to, polyvinyl alcohol, povidone, hydroxypropyl methyl cellulose, poloxamers, carboxymethyl cellulose, hydroxyethyl cellulose, and purified water.

Tonicity adjustors may be added as needed or convenient. They include, but are not limited to, salts, particularly sodium chloride, potassium chloride, mannitol, and glycerin, or any other suitable ophthalmically acceptable tonicity adjustor.

Various buffers and means for adjusting pH may be used so long as the resulting preparation is ophthalmically acceptable. Accordingly, buffers include but are not limited to, acetate buffers, citrate buffers, phosphate buffers, and borate buffers. Acids or bases may be used to adjust the pH of these formulations as needed.

In a similar vein, ophthalmically acceptable antioxidants include, but are not limited to, sodium metabisulfite, sodium thiosulfate, acetylcysteine, butylated hydroxyanisole, and butylated hydroxytoluene.

Other excipient components which may be included in the exemplary ophthalmic preparation described in Table I are chelating agents which may be added as needed. The preferred chelating agent is edetate disodium, although other chelating agents may also be used in place of or in conjunction with it.

For treatment of ocular bleeding, which occurs, for example during conventional "invasive" ophtalmic surgery, and also during certain type of ocular surgery conducted with laser, the compounds of the present invention are also administered to the eye in a pharmaceutical composition which comprises, in addition to an effective concentration of one or more compounds of the invention (or of salts thereof), a suitable, pharmacologically acceptable carrier. Ophtalmic solutions and suspensions are preferred as carriers, and the concentrations of the active compound or compounds of the invention may be typically in the same range as for their use as anti-glaucoma agents. The ophtalmic solutions or suspensions are typically adjusted to isotonicity with sodium chloride, and thickening agents such as carboxymethylcellulose, or carbopol may also be employed to enhance delivery. The pH of the ophtalmic solution or suspension is typically also adjusted to be within ophtalmically acceptable range. The specification of U.S. Pat. No. 4,587,257, as it pertains to the utilization of compounds capable of treating or controlling intraocular bleeding, is hereby expressly incorporated by reference.

The anti-glaucoma activity (ability to maintain or reduce intraocular pressure) of the compounds of the present invention is established by the following assay pressure. This assay procedure is generally recognized in the art to provide pertinent information with respect to the anti-glaucoma activity of the formulations assayed. Thus, each of the compounds of the invention to be tested was dissolved in distilled water at a concentration of 0.3% (W/V). Each of these solutions was administered topically and unilaterally to one eye of a drug-naive, unanesthetized monkey or New Zealand white rabbit in a single 50 micro liter drop. The contralateral eye received an equal volume of saline prior to determining the intraocular pressure after the mixture was administered. Also, approximately 10 micro liters of 0.5% (W/V) proparacaine (topical anesthetic) was applied to the corneas of each of the animals before determining intraocular pressure. As a control test, six (6) other drug-naive, unanesthetized animals were treated and tested as described above except that no compound of the invention was included in the solutions administered to the eyes.

The intraocular pressure was determined in both eyes of each animal both before and after the solutions were administered. Such intraocular pressure determinations were made in the conventional manner using conventional equipment.

Results of these IOP determinations were as follows:

| | Maximum Difference in Intraocular Pressure After Solution Administration % Decrease in IOP from Control (Duration hours) | |
| --- | --- | --- |
| Example | Ipsilateral (Treated) Eye | Contralateral (Untreated) Eye |
| Control | 0.0 ± 1.4 | 0.5 ± 1.2 |
| Example 31 | 14 ± 2.5 | 6.8 ± 1.8 |

| Example | Maximum Difference in Intraocular Pressure After Solution Administration % Decrease in IOP from Control (Duration hours) | |
| --- | --- | --- |
| | Ipsilateral (Treated) Eye | Contralateral (Untreated) Eye |
| Example 22 | (1–6 h) 11.5 ± 2.7 (1–2 h) | (1 h) 5.7 ± 2.0 (1 h) |

N.S. refers to no significant change in the intraocular pressure.

These results demonstrate the effectiveness in reducing intraocular pressure achieved by directly administering the compounds of the invention to mammalian eyes.

The vasoconstrictive properties of the compounds of the present invention, i.e. their ability to reduce or control intraocular bleeding, are established by the rabbit aorta: alpha 1 adrenergic receptors in vivo assay procedure, which is recognized in the art to be indicative of the in vivo activity of the tested compounds as vasoconstrictors or as anti intraocular bleeding agents.

Thoracic aorta specimens were obtained form albino rabbits that were killed by $CO_2$ inhalation. The aorta was cut into 3 mm rings. Tissues were placed in Krebs-Hensleit solution of the following composition (millimolar): NaCl 119; KCl 4.7; $MgSO_4$ 1.5, $KH_2 PO_4$ 1.2; $CaCl_2$ 2.5; $NaHCO_3$ 25 and glucose 11.0. The solution also contained cocaine (0.1 millimolar) to block neuronal uptake and EDTA (30 micromolar) and ascorbic acid (5 micromolar) to prevent oxidation of the compound being tested. Tissues were hung in 10 ml organ baths and tension was measured via Grass FT03 force-displacement transducers. Resting tension was 2 g for the aorta. The solution was gassed with 95% $O_2$ and 5% $CO_2$ and maintained at 37° C. Tissues were allowed to equilibrate for 2 hours before stimulation and the cumulative addition of the compound to be tested (aryl oxazoline) was started. Tissue stimulation was performed using a square wave stimulator (WPI A310) Accupulser with A385 stimulus) at 0.1 Hz, 2 ms pulse width at 90 mA.

The results of these tests with regard to some examples of the compounds of the invention, are indicated as follows:

| Rabbit Aorta: Alpha 1 adrenergic receptor assay | |
| --- | --- |
| | $EC_{50}$ (nm) |
| Example 4 | 1120 ± 457 |
| Example 5 | 3.41 ± 0.5 |
| Example 7 | 39.0 ± 6.36 |
| Example 14 | >100,000 |
| Example 31 | 2740 ± 1430 |
| Example 22 | 1430 ± 891 |
| Example 56 | 1120 ± 94.1 |
| Example 50 | 940 ± 18.5 |
| Example 39 | 5690 ± 956 |
| L-phenylephrine* | 182.1 |

*control substance, Shayes and Green Journal of Pharmacology and Experimental Therapeutics; 1971 Vol 180 pp 317–325

The test procedure for alpha-2 adrenergic receptor activity of the compounds of the present invention is the rabbit vas deferens assay which is described as follows:

New Zealand white rabbits (2–3 kg) were killed by $CO_2$ inhalation and the vasa deferentia removed. The prostatic ends of the vasa deferentia (2–3 cm lengths) were mounted between platinum ring electrodes in 9 ml organ baths and bathed in Krebs bicarbonate solution of the following composition (millimolar): NaCl 118.0; KCl 4.7; $CaCl_2$ 2.5; $MgSO_4$ 1.2; $KH_2 PO_4$ 1.2; glucose 11.0; $NaHCO_3$ 25.0; which solution was maintained at 35 degrees C and bubbled with 95% $O_2$ and 5% $CO_2$. The initial tension of the vas deferens was 0.5 g. The tissues were left to equilibrate for 30 minutes before stimulation was started. Vasa were then field stimulated (0.1 Hz, 2 ms pulse width at 90 mA) using a square wave stimulator (WPI A310 Accupulser with A385 stimulus). the contractions of the tissue were recorded isometrically using Grass FTO3 force-displacement transducers and displayed on a Grass Model 7D polygraph. Cumulative concentration-response curves were obtained for the compounds being tested with a 4 minute contact time at each concentration. The reduction in response height was measured and expressed as a percentage of the height of the response before the addition of the compounds. Concentration response curves for each of the compounds were plotted. The effective concentration required for a 50% reduction in response height, expressed as $EC_{50}$ were obtained from these curves.

| Rabbit Vas Deferens Assay | | |
| --- | --- | --- |
| | $EC_{50}$ (nm) | Comment |
| Example 4 | 167 ± 56.1 | $\alpha_2$ Selective |
| Example 5 | 0.59 ± 0.14 | Non-Selective Potent-Vasoconstrictor |
| Example 7 | >10,000 | $\alpha_1$ Selective |
| Example 14 | 48.5 ± 20.6 | $\alpha_2$ Selective |
| Example 31 | 41.5 ± 24.4 | $\alpha_2$ Selective |
| Example 22 | 105 ± 35.5 | $\alpha_2$ Selective |
| Example 56 | 18.1 ± 1.21 | $\alpha_2$ Selective |
| Example 50 | 8.92 ± 3.11 | $\alpha_2$ Selective |
| Example 39 | 74.6 ± 43.6 | $\alpha_2$ Selective |

SPECIFIC EMBODIMENTS

The compounds of this invention can be made by a number of different synthetic chemical pathways. To illustrate this invention, there is here outlined a series of steps which have been proven to provide the compounds of Formula 1 when such synthesis is followed in fact and in spirit. The synthetic chemist will readily appreciate that the conditions set out here are specific embodiments which can be generalized to any and all of the compounds represented by Formula 1. Furthermore, the synthetic chemist will readily appreciate that the herein described synthetic steps may be varied and or adjusted by those skilled in the art without departing from the scope and spirit of the invention.

Thus, the 1,4-benzoxazine derivatives of the present invention (compounds of Formula 1) can be made in accordance with the generalized synthetic procedures illustrated below. Specifically, the 1,4-benzoxazine derivatives of the present invention which are substituted with the 2-imino-2-imidazolidine group in the 7 position of the 1,4-benzoxazine nucleus are made in accordance with Reaction Scheme 1. In accordance with this procedure, 2-amino-5-nitrophenol (available commercially) is reacted with ethyl 2-bromoacetate to provide 7-nitro-3-oxo-3,4-dihydro-(2H)-1,4-benzoxazine (Compound 1). (In the present description the terms "compound" and "example" are sometimes used interchangeably, with the proper meaning being readily ascertainable from the context. The numerals following these terms are not used in duplicate, so that the term "Compound 1" refers to the same compound as "Example 1"). 7- nitro-3-oxo-3,4-dihydro-(2H)-1,4-benzoxazine (Compound 1) is reduced to provide 7-amino-3-oxo-3,4-dihydro-(2H)-1,4-benzoxazine (Compound 2). 7-amino-3-oxo-3,4-dihydro-(2H)-1,4-benzoxazine (Compound 2) is a compound described in *J. Med. Chem.* 1989, 32, 1627–1630. The 2-imino-2-imidazolidine group is then introduced into the 7 position of the 1,4-benzoxazine nucleus by reaction Compound 2 with 2-imidazoline sulfonic acid to provide 7-2(2-imino-2-imidazolidine)-3-oxo-3,4-dihydro-(2H)-1,4-benzoxazine (Compound 3). Compound 3 is also mentioned in the above-noted *J. Med. Chem.* reference. Although 2-imidazoline-sulfonic acid is a known compound, its preparation from 2-imidazolidinethione is described in detail below.

Referring now to Reaction Scheme 2, the 7-2(2-imino-2-imidazolidine) compounds of the invention which are bromo substituted can be made by bromination of 7-2(2-imino-2-imidazolidine)-3-oxo-3,4-dihydro-(2H)-1,4-benzoxazine (Compound 3) to provide a 6-monobromo derivative (Compound 4) and a 6,8-dibromo derivative (Compound 5). 8-Bromo-7-2(2-imino-2-imidazolidine)-3-oxo-3,4-dihydro-(2H)-1,4-benzoxazine (Compound 6, not shown on Reaction Scheme 2) can be made by reacting 8-Bromo-7-amino-3-oxo-3,4-dihydro-2H-1,4-benzoxazine with 2-imidazoline-sulfonic acid. Compound 3, as well as its bromo derivatives, such as Compounds 4, 5 and 6 are reduced with LiAlH$_4$ to remove the 3-oxo group, and to provide the

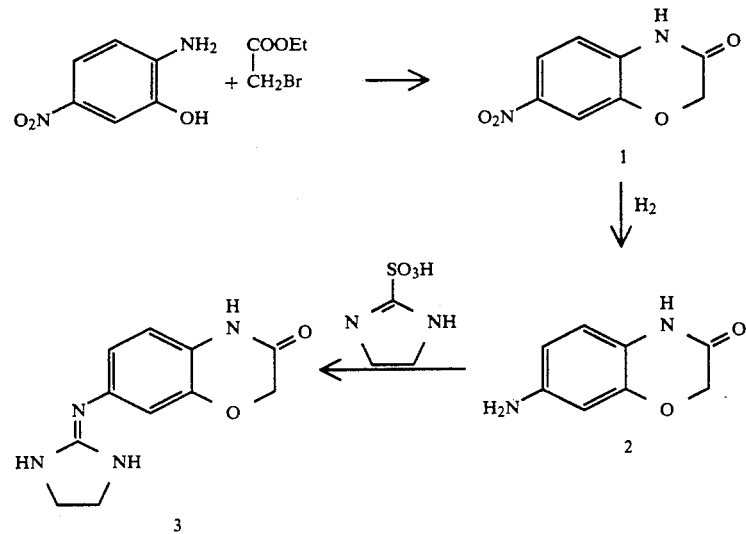

REACTION SCHEME 1 compounds, (for example Compounds 7 and 8) where, with reference to Formula 1, R$_2$ is hydrogen.

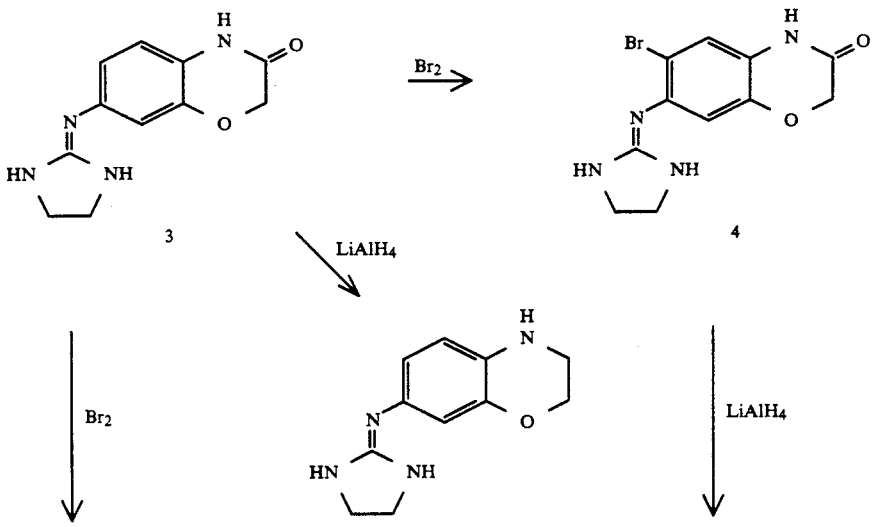

Reaction Scheme 2

Reaction Scheme 2

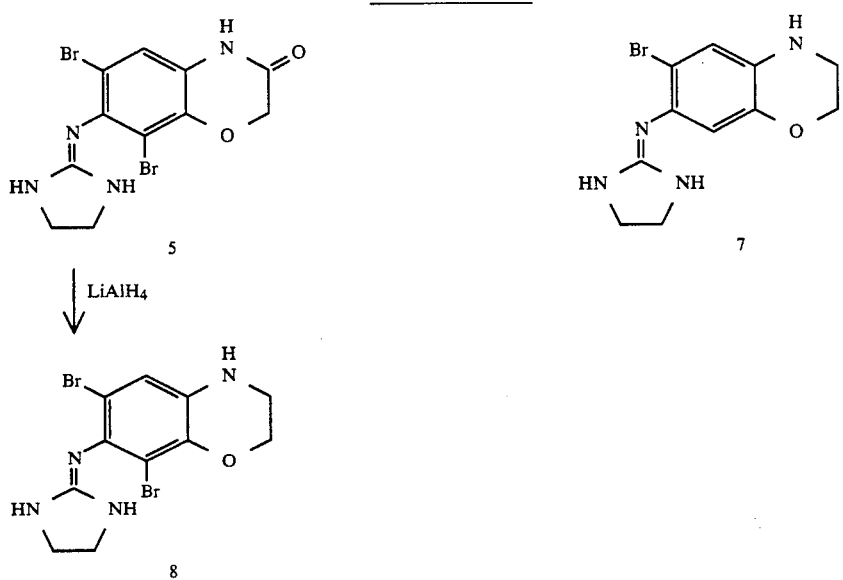

With reference to Reaction Scheme 3, in order to obtain the 4-N-alkyl substituted 7-2(2-imino-2-imidazolidine)-substituted compounds of the invention, 7-nitro-3-oxo-3,4-dihydro-(2H)-1,4-benzoxazine (Compound 1) is alkylated in the presence of strong base (such as NaH). The resulting 4-N-alkyl derivative (Compound 19 when the alkyl group is methyl) is reduced to provide 7-amino-4-methyl-3-oxo-3,4-dihydro-2H-1,4-benzoxazine (Compound 20), which is then reacted with 2-imidazoline-sulfonic acid to give 4-methyl-7-2(2-imino-2-imidazolidine)-3-oxo-3,4-dihydro-(2H)-1,4-benzoxazine (Compound 21). It will be readily understood by those skilled in the art that whereas Reaction Scheme 3 shows $CH_3I$ as the alkylating agent, the alkylation reaction disclosed here by this example is not so limited. 4-methyl-7-2(2-imino-2-imidazolidine)-3-oxo-3,4-dihydro-(2H)-1,4-benzoxazine (Compound 21) is brominated to yield 6-bromo-4-methyl-7-2(2-imino-2-imidazolidine)-3-oxo-3,4-dihydro-(2H)-1,4-benzoxazine (Compound 22) and 6,8-dibromo-4-methyl-7-2(2-imino-2-imidazolidine)-3-oxo-3,4-dihydro-(2H)-1,4-benzoxazine (Compound 24). The 4-N-alkyl-7-2(2-imino-2-imidazolidine)-3-oxo-3,4-dihydro-2H-1,4-benzoxazines, such as 4-methyl-7-2(2-imino-2-imidazolidine)-3-oxo-3,4-dihydro-2H-1,4-benzoxazine, (Compound 21) are reduced with lithium aluminum hydride (or similar reagent) to remove the 3-oxo function and yield the compounds, where, with reference to Formula 1, $R_2$ are hydrogen.

When the 4-N substituent is methyl, 4-methyl-7-2(2-imino-2-imidazolidine)-3,4-dihydro-(2H)-1,4-benzoxazine is obtained in this reaction. Similar removal of the 3-oxo groups by reduction with $LiAlH_4$ can be performed on the 4-N-alkyl bromo derivatives; for example reduction with $LiAlH_4$ of Compound 22 and Compound 24 provides 6-bromo-4-methyl-7-2(2-imino-2-imidazolidine)-3,4-dihydro-(2H)-1,4-benzoxazine (Compound 23) and 6,8-dibromo-4-methyl-7-2(2-imino-2-imidazolidine)-3,4-dihydro-(2H)-1,4-benzoxazine (Compound 25), respectively.

Reaction Scheme 3

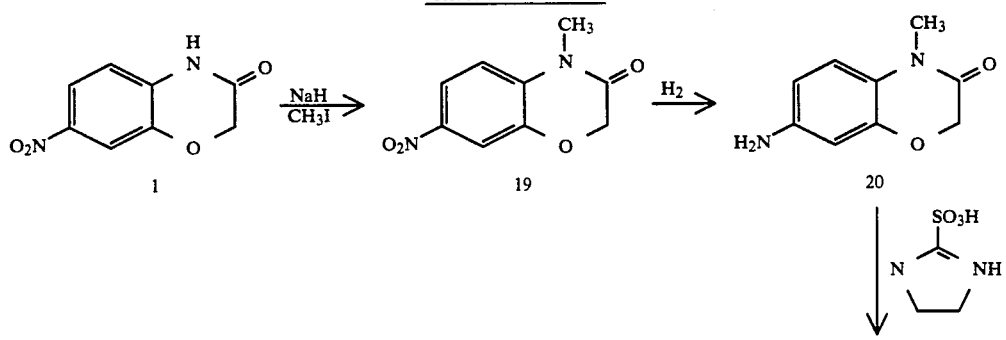

-continued
Reaction Scheme 3

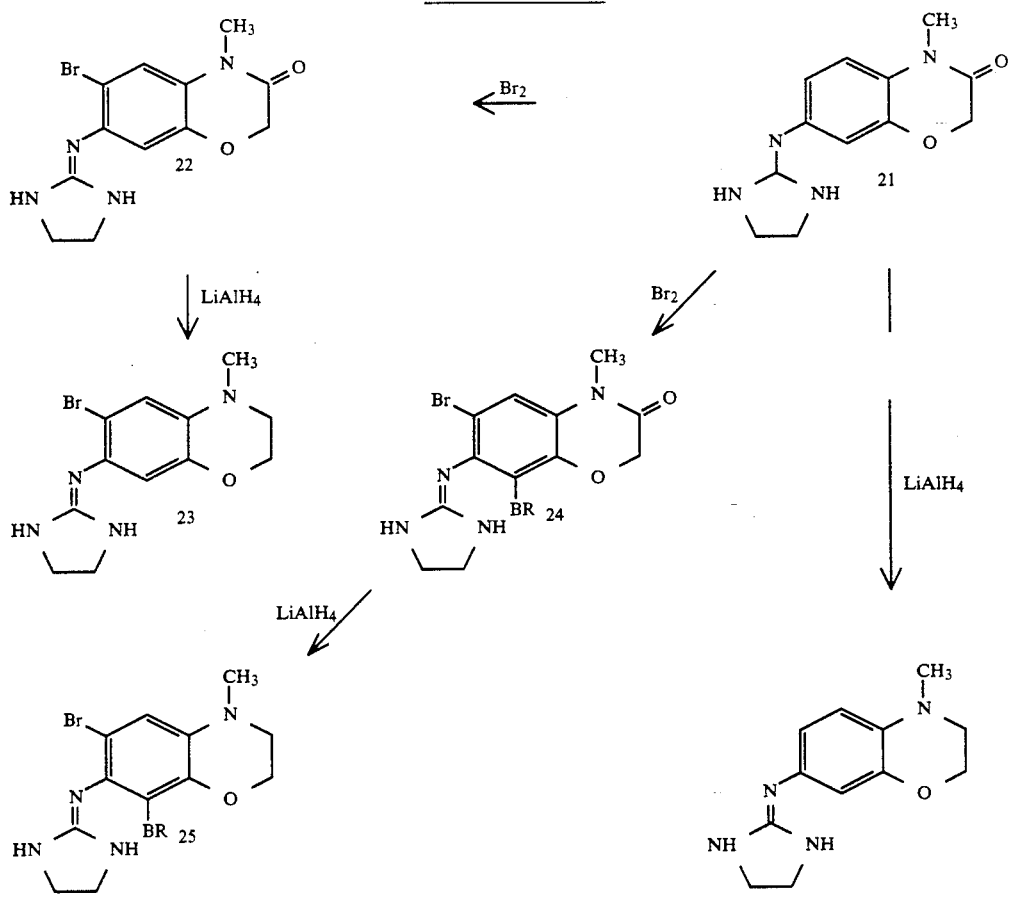

The 2-alkyl substituent can be introduced into the compounds of the present invention by using, in the condensation reaction involving 2-amino-5-nitrophenol (Reaction Scheme 1) an appropriate "alkylated" derivative of ethyl bromoacetate. For example, by using ethyl 2-bromopropionate in this reaction the 2-methyl derivatives of the compounds of the invention can be obtained.

The 1,4-benzoxazine derivatives of the present invention which are substituted with the 2-imino-2-imidazolidine group in the 6 position of the 1,4-benzoxazine nucleus are made in synthetic steps which are analogous to the synthetic steps generally described above. Thus, in accordance with Reaction Scheme 4, 2-amino-4-nitrophenol (available commercially) is reacted with ethyl 2-bromoacetate to provide 6-nitro-3-oxo-3,4-dihydro-(2H)-1,4-benzoxazine (Compound 10). 6-nitro-3-oxo-3,4-dihydro-(2 H)-1,4-benzoxazine (Compound 10) is reduced to provide 6-amino-3-oxo-3,4-dihydro-(2H)-1,4-benzoxazine (Compound 11), which is thereafter reacted with 2-imidazoline sulphonic acid to yield 6-2(2-imino-2-imidazolidine)-3-oxo-3,4-dihydro-(2H)-1,4-benzoxazine (Compound 12). Compound 10, Compound 11 and Compound 12, per se, are known (see the above-cited J. Med. Chem. article).

Reaction Scheme 4

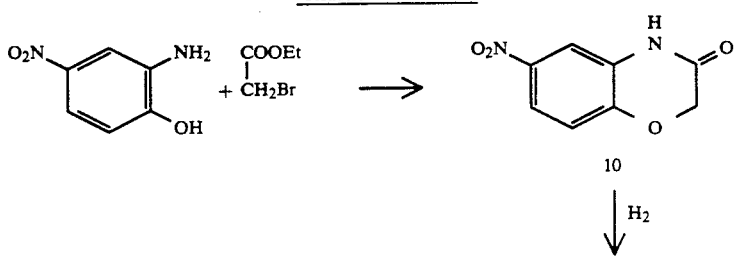

Reaction Scheme 4

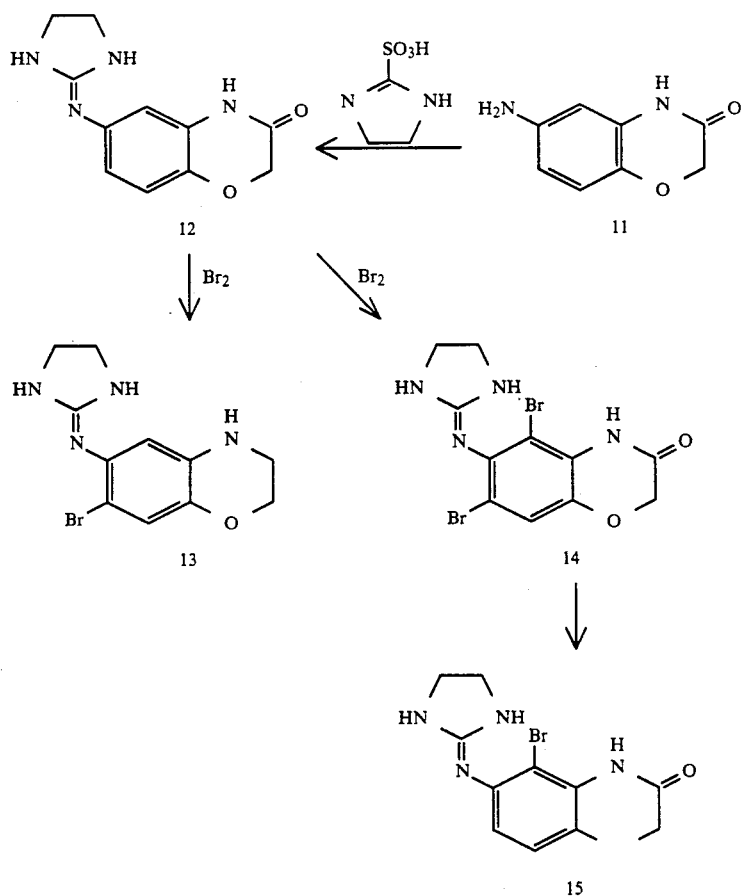

The herein relevant synthetic steps performed respectively on 6-nitro-3-oxo-3,4-dihydro-(2H)-1,4-benzoxazine (Compound 10) on 6-2(2-imino-2-imidazolidine)-3-oxo-3,4-dihydro-2H-1,4-benzoxazine (Compound 12) and on other analogs where the nitro, amino and/or 2-imino-2-imidazolidine substituent is on the 6 position of the 3,4-dihydro-1,4-benzoxazine nucleus, (rather than on the 7 position of the same nucleus), are substantially similar to the synthetic steps described above for the 7-substituted analogs. For this reason these synthetic steps are not detailed here further. It is noteworthy, however, still with reference to Reaction Scheme 4 that monobromination of 6-2(2-imino-2-imidazolidine)-3-oxo-3,4-dihydro-2H-1,4-benzoxazine (Compound 12) yields the corresponding 7-bromo derivative (Compound 13), dibromination yields the corresponding 5,7-dibromo derivative (Compound 14), and that the 5,7-dibromo derivative (Compound 14) can be selectively debrominated to yield the corresponding 5-bromo derivative (Compound 15).

Reaction Scheme 5

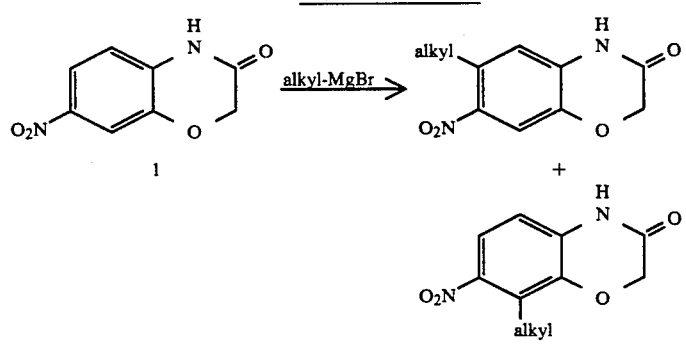

Reaction Scheme 5

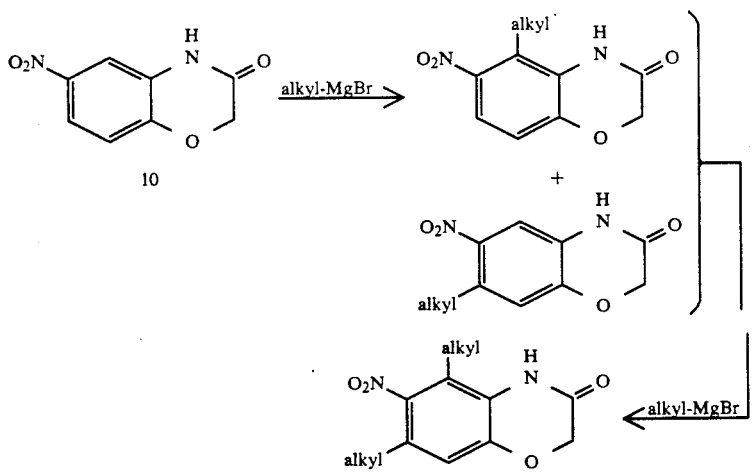

The $R_4$, $R_5$ and $R_6$ substituents (preferably lower alkyl of 1-3 carbons or lower alkenyl of 1-3 carbons such as allyl) are introduced into the compounds of the invention by reacting the 7-nitro-3-oxo-3,4-dihydro-(2H)-1,4-benzoxazine intermediate (Compound 1) and the 6-nitro-3-oxo-3,4-dihydro-(2H)-1,4-benzoxazine intermediate (Compound 10) with an excess of a Grignard reagent. (Reaction Scheme 5).

When the starting material is Compound 10, then 5 and 7 C-alkyl substituted reaction products are obtained. The 5,7 dialkyl substituted product is obtained by further alkylation. These C-alkyl substituted compounds are carried through the reaction sequences described above (to wit: reduction of nitro group to amino group, subsequent condensation with 2-imidazoline sulphonic acid, and reduction of the 3-oxo group or in the alternative N-alkylation followed by reduction of the nitro group etc.) to provide the C-alkyl and dialkyl substituted compounds of the invention. When the starting material is 7-nitro-3-oxo-3,4-dihydro-2H-1,4-benzoxazine intermediate (Compound 1), then the reaction with the Grignard reagent yields 6 and 8 mono C-alkyl derivatives, which can also be carried through the above-noted reaction sequences to yield the 6 or 8 alkyl (or alkenyl) substituted 7-2(2-imino-2-imidazolidine)-3,4-dihydro-(2H)-1,4-benzoxazine derivatives of the present invention.

SPECIFIC EXAMPLES

EXAMPLE 1

7-nitro-3-oxo-3,4 dihydro-(2H)-1,4-benzoxazine

Under argon, ethyl bromoacetate (7.2 ml, 65 mmol) was added to a solution of anhydrous potassium fluoride (10 g, 172.1 mmol) in 50 ml anhydrous DMF. The solution was stirred for 30 minutes at room temperature. 2-Amino-5-nitrophenol (Aldrich, 10 g, 65 mmol) was then dissolved in 25 ml of DMF and added dropwise to the reaction with stirring. After the final addition the reaction was warmed to 70 degrees and stirred for 16-24 hours. The reaction was then poured into 300 mls of an ice/water mixture with stirring. A yellow precipitate was formed immediately. The solid was filtered off and dried in vacuo. The product was recrystallized from hot THF. Collected 8.3 g (72.5%) of tan crystals: m.p. 227-230; 'H NMR (300 MHz, DMSO) δ 4.752 (s, 2H, CH₂), 7.0835 (d, J=8.73, Hz, 1H, ACH), 7.769 (d, J=2.44 Hz, 1H) 7.9185 (dd, J=2.525, 8.705 Hz, 1H, ACH); ¹³C NMR (300 MHz, DMSO) δ 66.560, 111.344, 115.776, 118.738, 134.464, 142.643, 142.861, 164.891. Mass spectrum (EI) m/z 194 M+

EXAMPLE 2

7-amino-3-oxo-3,4-dihydro-(2H)-1,4-benzoxazine

Under argon, 10% palladium on carbon (350 mg, 5% w/w) was added to a suspension of 7-nitro-3-oxo-3,4-dihydro-(2H)-1,4-benzoxazine (7 g, 39.3 mmol) in 50 ml of MeOH. The reaction mixture was hydrogenated at 40 psi for 16 hours. The reaction mixture was then diluted with THF (−200 mls) and the reaction was filtered through celite. The solvent was evaporated, leaving a brown solid as the residue. Product was recrystallized from THF/Hexane (1:5). Collected 4.2 g (72%) of a tan solid: m.p. 213-215, 'H NMR (300 M Hz, DMSO) δ 4.410 (S, 2H), 4.869 (S, 2H) 6.141 (d, 1H, J=2.44) 6.176 (dd, 1H, J=2.25, 4.69), 6.563 (d, 1H, J=8.19), 9.535 (brs, 1H); ¹³C NMR (300 MHz, DMSO) δ 66.9496, 102.2081, 108.1369, 116.5779; 116.8982, 144.5502, 145.4287, 164.389; Mass spectrum M+ at m/z 164

EXAMPLE 3

7-2(2-imino-2-imidazolidine)-3,4-dihydro-2H-1,4-benzoxazine 7-amino-3-oxo-3,4-dihydro-(2H)-1,4-benzoxazine (50 mg, 0.205 mmol) was combined with 2-imidazoline sulfonic acid (62 mg, 0.410 mmol) in 5 ml isobutanol. The reaction was heated to 50 degrees for 16 hours. The solvent was evaporated leaving a yellow solid. The product was purified by flash chromatography (70:30, CHCl₃: MeOH sat. with NH₃) and product was isolated as a white solid (23.2 mg, 49%) m.p. 271-275 (decomp.); H NMR (300 MHz, DMSO) δ 3.587 (S, HH, 4.560 (S, 2H, 6.755 (m, 2H), 6.918 (d, 2H, J=8.03) −C NMR (300 MHZ, DMSO) δ 42.7154, 66.9089, 111.6185, 116.6721, 117.4629, 125.5162, 132.0013, 144.0188, 158.6280, 164.9108; mass spectrum (EI) M+ observed at m/z 232.

EXAMPLE 4

6-Bromo-7-(2-imino-2-imidazolidine)-3-oxo-3,4-dihydro-(2H)-1,4-benzoxazine, hydrobromide A solution of 7-(2-imino-imidazolidine)-3-oxo-3,4-dihydro-(2H)-1,4-benzoxazine (100 mg; 0.430 mmol) in acetic acid (2 ml) at room temperature was treated with $H_2SO_4$ (1 drop) followed by dropwise addition of bromine (688 mg, 4.30 mmol). The reaction was stirred at room temperature for 16 hours. The title compound was obtained as a yellow crystalline solid which was washed with ether and dried in vacuo. Yield: 164.3 mg (100%); mp 220–230 degrees C., decomp; $^1$H NMR (300 MHz, DMSO) δ 10.51 (br, 3H); 6.98 (s, 1H); 6.52 (s, 1H).

EXAMPLE 5

6,8-dibromo-7-(2-imino-2-imidazolidine)-3-oxo-3,4-dihydro-(2H)-1,4-benzoxazine

Procedure: 7-(2-imino-2-imidazolidine)-3-oxo-3,4-dihydro-(2H)-1,4-benzoxazine (100 mg, 0.430 mmol) was dissolved in 2 ml of AcOH. One drop of $H_2SO_4$ was added and the reaction mixture was heated to reflux for 16 hours. The reaction mixture was cooled, basified to pH 14 with 2.5 N NaOH and extracted with ethyl acetate. Extracts were dried and evaporated leaving a tan solid. Purified by flash chromatography ($SiO_2$, $NH_3$ sat. MeOH: $CHCl_3$, 5:95) to give a yellow solid. Collected 115.4 mg(69%) of product; mp 254-255; Mass spectrum m/z, $M^+$ observed at 388, 390 and 392; High resolution Mass spectrum calculated for $C_{11}H_{10}N_4O_2Br_2$ 387.9170, found 387.9152; calc'd for $C_{11}H_{10}N_4O_2{}^{81}BrBr$ 389.9150, found 389.9145; calc'd for $C_{11}H_{10}N_4O_2{}^{81}Br_2$ 391.9129, found 391.9138.

EXAMPLE 6

8-bromo-7-(2-imino-2-imidazolidine)-3-oxo-3,4-dihydro-(2H)-1,4-benzoxazine

Procedure: 8-bromo-7-amino-3-oxo-3,4-dihydro-(2H)-1,4-benzoxazine (100 mg, 0.411 mmol) and 2-imidazoline-2-sulfonic acid (92 mg, 0.616 mmol) was suspended in 5 mls of i-BuOH and heated to reflux for 16 hours. The reaction mixture was basified to pH 14 with 2N NaOH and extracted with EtOAC. The combined extracts were dried ($MgSO_4$) and evaporated leaving a tan solid. Product was purified by flash chromatography ($SiO_2$, $NH_3$ sat. MeOH: $CHCl_3$, 5:95) collected 66.4 mg (50%) of an off-white solid. mp 205-215 (decomp); $^1$H NMR (300 MHz, DMSO) δ 10.4 (brs, 1H); 6.63 (d, 1H); 6.40 (d, 1H); 5.10 (brs, 2H); 4.55 (s, 2H); 3.31 (s, 4H); Mass spectrum m/z, $M^+$ 310, 312; High resolution mass spectrum, calculated for $C_{11}H_{11}N_4O_2Br$ 310.005, found 310.0065.

EXAMPLE 7

6-bromo-7-(2-imino-2-imidazolidine)-3,4-dihydro-(2H)-1,4-benzoxazine

A solution of 6-bromo-7-(2-imino-2-imidazolidine)-3-oxo-3,4-dihydro-(2H)-1,4-benzoxazine (310 mg, 1 mmol) in tetrahydrofuran (4 ml) is treated with $LiAlH_4$ (38 mg, 1 mmol) and the reaction mixture is heated at reflux for 1 hour. The reaction is cooled to room temperature, filtered through celite and concentrated in vacuo to yield a residue which is chromatographed ($SiO_2$; $CHCl_3/CH_3OH$ saturated with $NH_3$) to yield the title compound which is characterized spectroscopically.

EXAMPLE 8

6,8-Dibromo-7-(2-imino-2-imidazolidine)-3,4-dihydro-(2H)-1,4-benzoxazine

The title compound is prepared by $LiAlH_4$ mediated reduction of 6,8-dibromo-7-(2-imino-2-imidazolidine)-3-oxo-3,4-dihydro-(2H)-1,4- in tetrahydrofuran using the procedure illustrated in Example 7.

EXAMPLE 9

8-bromo-7-(2-imino-2-imidazolidine)-3,4-dihydro-(2H)-1,4-benzoxazine

The title compound is prepared by $LiAlH_4$ mediated reduction of 8-bromo-7-(2-imino-2-imidazolidine)-3-oxo-3,4-dihydro-(2H)-1,4-benz in tetrahydrofuran using the procedure illustrated in Example 7.

EXAMPLE 10

6-nitro-3-oxo-3,4-dihydro-(2H)-1,4-benzoxazine

The title compound was prepared using the method illustrated in Example 1.

Yield 8.2 g (73.2%) tan crystals: m.p. 233–235; $^1$H NMR (300 MHz, DMSO) δ 4.754 (s, 1H), 7.12 (d, J=8.9 Hz, 2H), 7.714 (d, J =2.66, 1H) 7.8155 (dd, J=2.71, 8.9 Hz, 1H), 11.064 (brS, 1H); $^{13}$C NMR (300 MHz, DMSO) δ 66.8619, 110.9932, 116.7802, 119.3719, 127.9445, 142.1591, 149.0456, 164.1843; mass spectrum (EI) m/z at 194.

EXAMPLE 11

6-amino-3-oxo-3,4-dihydro-(2H)-1,4-benzoxazine

Procedure: under argon, 10% Pd/C (20 mg, 5% w/w) was added to a suspension of 6-nitro-3-oxo-3,4-dihydro-(2H)-1,4-benzoxazine (4 g, 20.6 mmol) in 100 ml MeOH. The reaction was hydrogenated at 40 psi for 4 hours. The reaction mixture was diluted with THF (150 mls) and filtered through celite. The solvent was evaporated leaving a tan solid. The product was purified by recrystallization from THF/Hexane (1:5). Collected 2.4 g (70.5%) of product as a tan solid: m.p. 221–223; $^1$H NMR (300 MHz, DMSO) δ 4.360 (s, 2H), 4.823 (s, 2H), 6.102 (dd, 1H, J=2.55, 8.41), 6.159 (d, 1H, J=249), 6.609 (d, 1H, J=8.41), 10.461 (brS, 1H); $^{13}$C NMR (300 MHz, DMSO) δ 67.0407, 101.4895, 108.2861, 116.3699, 127.6622, 134.1601, 144.1535, 165.7326; Mass spectrum M+ at M/Z 164.

EXAMPLE 12

6-(2-imino-2-imidazlidine)-3-oxo-3,4-dihydro-(2H)-1,4-benzoxazine

Procedure: 6-amino-3-oxo-3,4-dihydro-(2H)-1,4-benzoxazine (3.5 g, 21.3 mmol) was combined with 2-imidazoline sulphonic acid (6.4 g, 42.6 mmol) in 10 mls of i-BuOH. The reaction was heated to reflux for 16 hours. Ether was added and a white precipitate was formed. The solid was filtered and dried in vacuo. The solid is very hygroscopic so filtration was done quickly. The solid was then dissolved in $NH_3$ sat. MeOH and purified by flash chromatography ($SiO_2$, $NH_3$ sat. MeOH: $CHCl_3$, 30:70). Collected 4.05 g (82%) of product as a white solid; mp 225-230 (decomp); $^1$H NMR (300 MHz, DMSO) δ9.85 (br, 1H); 8.25 (br, 2H); 6.85 (d, 1H); 6.71 (d, 1H); 6.60 (m, 1H); 4.50 (s, 2H); 3.42 (s, 4H); $^{13}$C NMR (75 MHz, DMSO) δ 165.439, 158.417, 139.647, 127.929, 117.468, 116.667, 110.652, 66.900, 42.847; MS, M+ found at m/z 232.

EXAMPLE 13

7-bromo-6-(2-imino-2-imidazolidine)-3-oxo-3,4-dihydro-(2H)-1,4-benzoxazine hydrobromide Procedure: 6-(2-imino-imidazolidine)-3-oxo-3,4-dihydro-(2H)-1,4-benzoxazine (60 mg, 0.258 mmol) was dissolved in 2 ml AcOH. Br$_2$ (412 mg, 2.58 mmol) was added. The reaction mixture was stirred at room temperature for 4 hours. Diethyl ether was added, and an oil precipitated out from the reaction mixture. The diethyl ether was decanted off and the oil was dissolved in MeOH. Diethyl ether was added and the product precipitated as a yellow solid. No further purification was necessary. m.p. 230–235 decomp; $^{13}$C NMR (75 MHz, DMSO) δ 164.624, 158.856, 143.900, 128.219, 128.024, 120.524, 116.205, 114.283, 66.794, 42.732; MS M+ was found at m/z 310/312; High resolution mass spectrum: calc'd for $C_{11}H_{11}N_4O_2{}^{81}Br$ 312.0045, found 312.0044.

EXAMPLE 14

5,7-dibromo-6-(2-imino-2-imidazolidine)-3-oxo-3,4-dihydro-2H-1,4-benzoxazine

The title compound was prepared using the method illustrated in Example 5.

Yield 92.8 mg (55.6%); mp, 215–230 decomp; $^1$H NMR (300 MHZ, DMSO)δ 9.7 (br s, 1H), 7.2 (s, 1H), 6.1 (br S, 1H), 4.50 (s, 2H), 3.326 (s, 4H); $^{13}$CNMR (75 MHz, DMSO) S 165.794, 157.755, 144.183, 139.402, 126.761, 118.923, 111.097, 107.440, 67.133, 41.743; Mass spectrum: M+ found at m/z 388/390/392

EXAMPLE 15

5-bromo-6-(2-imino-2-imidazolidine)-3-oxo-3,4-dihydro-(2H)-1,4-benzoxazine

The title compound is prepared by debromination of 5,7-dibromo-6-(2-imino-2-imidazolidine)-3-oxo-3,4-dihydro-(2H)-1,4-benzoxazine (75 mg, 0.192 mmol) using (Ph3P)4Pd (236 mg, 0.19 mmol) and sodium formate (32 mg, 0.46 mmol) in dimethylformamide (4 ml). The reaction mixture is heated to 125 degrees C for 4 hours before cooling to room temperature and quenching with saturated NaHCO$_3$. The reaction mixture is extracted with ethyl acetate. The combined organic extracts are dried over MgSO$_4$ and concentrated in vacuo. The residue is chromatographed (SiO$_2$; CHCl$_3$; CH$_3$OH saturated with NH$_3$) to yield the title compound which is characterized spectroscopically.

EXAMPLE 16

7-bromo-6-(2-imino-2-imidazolidine)-3,4-dihydro-(2H)-1,4-benzoxazine

Procedure: 7-bromo-6-(2-imino-2-imidazolidine)-3-oxo-3,4-dihydro-(2H)-1,4-benzoxazine (112.7 mg, 0.362 mmol) was dissolved in 5 mls THF. LiAlH$_4$ (6.3 mg, 0.181 mmol, 2 equiv. of hydride) was added with stirring. The reaction mixture was heated to reflux and stirred for 16 hours whereafter it was cooled, quenched with a few drops of water and filtered through celite. The reaction mixture was then dried over MgSO$_4$ and evaporated leaving a yellow oil. The product was purified by flash chromatography (SiO$_2$; NH$_3$, MeOH: CHCl$_3$, 15:85). Collected 87.4 mg (85%) of a tan solid. m.p. 150–152; $^1$H NMR (300 MHZ, CDCl$_3$) δ 6.945 (s, 1H), 6.306 (s, 1H), 4.188 (t, 2H), 3.501 (s, 4H) 3.374 (t, 2H); $^{13}$C NMR (300 MHZ, CDCl$_3$) δ 40.889, 42.529, 65.112, 105.678, 110.424, 120.239, 133.521, 142.016, 147.2204, 158.006; Mass spectrum: M+ found at m/z 296; HRMS calculated for $C_{11}H_{13}N_4O$ Br 296.0272 found 296.0287

EXAMPLE 17

5,7-dibromo-6-(2-imino-2-imidazolidine)-3,4-dihydro-(2H)-1,4-benzoxazine

The title compound is prepared by LiAlH$_4$ mediated reduction of 5,7-dibromo-6-(2-imino-2-imidazolidine)-3-oxo-3,4-dihydro-(2H)-1,4-benzoxazine in tetrahydrofuran using the procedure illustrated in Example 7.

EXAMPLE 18

5-bromo-6-(2-imino-2-imidazolidine)-3,4-dihydro-(2H)-1,4-benzoxazine

The title compound is prepared by LiAlH$_4$ mediated reduction of 5-bromo-6-(2-imino-2-imidazolidine)-3-oxo-3,4-dihydro-(2H)-1,4-benzoxazine in tetrahydrofuran using the procedure illustrated in Example 7.

EXAMPLE 19

4-methyl-7-nitro-3-oxo-3,4-dihydro-(2H)-1,4-benzoxazine

Procedure: 7-nitro-3-oxo-3,4-dihydro-(2H)-1,4-benzoxazine (3.57 g, 18.4 mmol) was dissolved in 200 mls of dry THF. 60% NaH (736 mg 18.4 mmol) was added, with stirring at room temperature. The reaction was stirred for 0.5 hours. CH$_3$I (2.3 ml, 36.8 mmol) was added dropwise. After the final addition, the reaction was heated to reflux for 2 hours. Then the reaction mixture was cooled and quenched with H$_2$O, and thereafter was extracted with CHCl$_3$. The combined extracts were dried (MgSO$_4$) and evaporated leaving a tan oil. The desired product was collected as a tan solid (2.6 g 68%). M.P. 183–185; $^1$H NMR (300 MHZ, DMSO) and 7.96 (dd, J=9.01 Hz, 1H), 7.781 (d, J=2.49 Hz, 1H), 7.36 (d, J=8.95, 1H), 4.796 (s, 1H), 3.322 (S, 3H); $^{13}$C NMR (300 MHZ, DMSO) and 28.047, 66.923, 111.469, 115.768, 118.778, 135.870, 142.813, 144.731, 164.282. Mass spectrum: M+ observed at m/z 208; HRMS calculated for $C_9H_8N_2O_4$ 208.0000, found 208.0484.

EXAMPLE 20

7-amino-4-methyl-3-oxo-3,4-dihydro-(2H)-1,4-benzoxazine

Procedure: 4-methyl-7-nitro-3-oxo-3,4-dihydro-2H-1,4-benzoxazine (2 g, 10.4 mmol) was dissolved in 50 ml MeOH. The solution was purged with argon for 15 minutes. 10% Pd/C (200 mg, 5% w/w) was added and the mixture was hydrogenated for 16 hours at 20 psi. The reaction mixture was filtered through celite and evaporated leaving a yellow oil. Product was purified by flash chromatography (SiO$_2$, NH$_3$, MeOH: CHCl$_3$, 5:95). Collected 1.4 g (78%) of a tan solid. MP 143–145; $^1$H NMR (300 MHZ, DMSO) and 6.81 (d, J=8.47, 1H) 6.237 (m, 2H), 5.000 (S, 2H), 4.490 (s, 2H), 3.170 (s, 3H) $^{13}$C NMR (300 MHz, DMSO and 27.4673, 67.2261, 102.2182, 108.0221, 116.0754, 119.2791, 145.7760, 145.9278, 163.4086. Mass spectrum: M+ observed a m/z 178; HRMS, calculated for $C_9H_{10}N_2O_2$, 178.000, found 178.0742.

EXAMPLE 21

4-methyl-7-(2-imino-imidazolidine)-3-oxo-3,4-dihydro-(2H)-1,4-benzoxazine.

Procedure: 4-methyl-7-amino-3-oxo-3,4-dihydro-(2H)-1,4-benzoxazine (55 mg, 0.295 mmol) was combined with 2-imidazoline sulfonic acid (88.5 mg, 570 mmol) in 5 ml of i-BUOH. The reaction was heated for 125 degrees C. for 16 hours. The reaction mixture was cooled, basified with 2.5N NaOH to pH 14, and extracted with EtoAC. The combined extracts were dried and evaporated leaving a yellow oil. Product was purified by flash chromatography ($SiO_2$, $CHCl_3$; $NH_3$, MeOH, 90:10). Collected 58.6 mg (34%) of a white solid. MP 251-254 (decomp); 'H NMR (300 MHZ, DMSO) and 6.95 (a, 1H); 6.62 (m, 2H); 6.20 (br, 2H); 4.52 (s, 2H); 3.30 (S, 4H); 3.20 (s, 3H); Mass spectrum: M+ m/z 246; High Resolution Mass Spectrum: calculated for $C_{12}H_{14}N_4O_2$ 246.1116; found 246.1106.

EXAMPLE 22

4-methyl-6-bromo-7-(2-imino-imidazolidine)-3-oxo-3,4-dihydro-2H-1,4-benzoxazinehydrobromide Procedure: 4-methyl-7-(2-imino-imidazolidine)-3-oxo-3,4-dihydro-(2H)-1,4-benzoxazine (100 mg, 0.406 mmol) was dissolved in 5 ml AcoH. $Br_2$ (77 microliter, 0.812 mmol) was added dropwise. A drop of $H_2SO_4$ was added and the reaction was stirred at room temperature for 16 hours. The reaction mixture was cooled to 0 degrees and diethyl ether was added. The product was isolated as the HBr salt. The product was recrystallized from MeOH: $Et_2O$ (5:1). Collected 132 mg (80%) of a white solid. M.P. >300—; 'H NMR (300 MHz, DMSO) and 10.180 (brS, 1H), 8.240 (br s, 2H), 7.524 (s, 1H), 7.176 (s, 1H), 4.707 (s, 2H), 3.632 (s, 4H), 3.284 (s, 3H); Mass spectrum: M+ m/z 324.326; High Resolution Mass Spectrum Calc'd for $C_{12}H_{13}N_4O_2Br$ 324.0222; found 324.0220; calc'd for $C_{12}H_{13}N_4O_2$ $^{81}Br$ 326.0201; found 326.0202.

EXAMPLE 23

6-bromo-4-methyl-7-(2-imino-imidazolidine)-3,4-dihydro-(2H)-1,4-benzoxazine.

Procedure: 6-bromo-4-methyl-7-(2-imino-imidazolidine)-3-oxo-3,4-dihydro-(2H)-1,4-benzoxazine (100 mg, 0.308 mmol) was dissolved in 10 ml of THF. $LiAlH_4$ (5.8 mg 0.154 mmol, 2 equiv. of hydride) was added with stirring at room temperature. The reaction was then heated to reflux for 4 hours. The reaction was quenched with $H_2O$ and extracted with EtoAc. The combined extracts were dried ($MgSO_4$) and evaporated leaving a tan oil. The product, was purified by flash chromatography (90:10, $CHCl_3$: $NH_3$, MeOH). Collected 42.8 mg (44.8%) of a tan solid. MP 194-198 decomp; 1H NMR (300 MHz, $CDCl_3$) and 6.809 (s, 1H), 6.518 (s, 1H), 4.580 (br S), 4.263 (t, 2H), 3.507 (s, 4H), 3.178, (t, 2H), 2.817 (s, 3H); $^{13}C$ NMR (300 MHz, $CDCl_3$) and 158.8009, 144.3704, 138.4333, 133.4388, 116.2412, 111.986, 109.7393, 65.0111, 48.8641, 42.3351, 38.8633; MS, M+ found at m/z 310; HRMS calculated for $C_{12}H_{15}N_4OBr$ 310.0429, found 310.0436.

EXAMPLE 24

6,8-Dibromo-4-methyl-7-(2-imino-2-imidazolidine)-3-oxo-3,4-dihydro-(2H)-1,4-benzoxazine, hydrobromide.

The title compound is prepared by treating a solution of 4-methyl-7-(2-imino-2-imidazolidine)-3-oxo-3,4-dihydro-(2H)-1,4-benzoxazine in acetic acid with bromine and a catalytic amount of $H_2SO_4$, using the method illustrated in Example 5.

EXAMPLE 25

6,8-Dibromo-4-methyl-7-(2-imino-2-imidazolidine)-3,4-dihydro-(2H)-1,4-benzoxazine. The title compound is prepared by $LiAlH_4$ mediated reduction of 6,8-dibromo-4-methyl-7-(2-imino-2-imidazolidine)-3-oxo-3,4-dihydro-(2H)-1,4-benzoxazine in tetrahydrofuran, using the procedure illustrated in Example 7.

EXAMPLE 26

8-Bromo-4-methyl-7-(2-imino-2-imidazolidine)-3-oxo-3,4-dihydro-(2H)-1,4-benzoxazine.

The title compound is prepared by debromination of 6,8-dibromo-4-methyl-7-(2-imino-2-imidazolidine)-3-oxo-3,4-dihydro(2H)-1,4-benzoxazine using the procedure illustrated in Example 15.

EXAMPLE 27

8-Bromo-4-methyl-7-(2-imino-2-imidazolidine)-3,4-dihydro-(2H)-1,4-benzoxazine.

The title compound is prepared by reduction of 8-bromo-4-methyl-7-(2-imino-2-imidazolidine)-3-oxo-3,4-dihydro-(2H)-1,4-benzoxazine using the procedure illustrated in Example 7.

EXAMPLE 28

4-methyl-6-nitro-3-oxo-3,4-dihydro-(2H)-1,4-benzoxazine

The title compound was prepared from 6-nitro-3-oxo-3,4-dihydro-(2H)-1,4-benzoxazine using the method described in Example 19. Yield: 3.01 g (56%) of product as a yellow solid. mp 185-187; 'H NMR (300 MHz, DMSO) and 7.968 (dd, J=8.9 Hz, 2H), 7.78 (d, J=2.5H 1H), 7.363 (d, J=8.9 2H), 4.799 (s, 2H), 3.32 (s, 3H); $^{13}C$ NMR (75 MHz, DMSO) and 164.430, 144.77, 135.913, 118.824, 115.808, 111.5142, 66.944, 20.82; Mass Spectrum M+ m/z 208.

EXAMPLE 29

6-amino-4-methyl-3-oxo-3,4-dihydro-(2H)-1,4-benzoxazine.

The title compound was prepared from 4-methyl-6-nitro-3-oxo-3,4-dihydro-(2H)-1,4-benzoxazine using the method described in Example 20

Yield: 1.3 g (72%) of a tan solid; mp 143-145; 'H NMR (300 MHz, DMSO) and 6.811 (d, J=8.46, 1H), 6.250 (m, 2H), 5.002 (s, 2H), 4.492 (s, 2H), 3.172 (s, 3H); $^{13}C$ NMR (25 MHz, DMSO) and 163.442, 145.958, 145.813, 119.296, 116.114, 108.043, 102.237, 67,251, 27.494; Mass spectrum: M+ m/z 178.

EXAMPLE 30

4-Methyl-6-(2-imino-2-imidazolidine)-3-oxo-3,4-dihydro-(2H)-1,4-benzoxazine.

The title compound was prepared from -6-amino-4-methyl-3-oxo-3,4-dihydro-(2H)-1,4-benzoxazine using the method described in Example 21. Yield 74.8 mg (58.8%) (as a white solid) M.P. 262-264; 'H NMR (300 MHz, DMSO) and 6.939 (d, J=8.9, 1H), 6.633 (m, 2H), 4.537 (s, 2H), 3.302 (s, 4H), 3.215 (s, 3H); $^{13}C$ NMR (300 MHz, DMSO) and 27.5584, 43.0360, 67.1992, 109.5818, 115.5611, 115.7735, 122.6263, 145.3208, 158.2961, 163.8386; MS, M+ found at m/z 246; HRMS calculated for $C_{12}H_{14}N_4O_2$ 246.1116 found 246.1131.

EXAMPLE 31

7-bromo-4-methyl-6-(2-imino-imidazolidine)-3-oxo-3,4-dihydro-(2H)-1,4-benzoxazine.

4-methyl-6-(2-imino-imidazolidine)-3-oxo-3,4-dihydro(2H)-1,4-benzoxaine was brominated, collected 110 mg (67%) of the product as a tan solid; mp 210–220 decomp; 'H NMR (300 MHz, DMSO) and 10.244 (s, 1H), 8.253 (s, 2H), 7.525 (s, 1H), 7.182 (s, 1H), 4.708 (s, 2H), 3.636 (s, 4H), 3.284 (s, 3H); $^{13}$C NMR (75 MHz, DMSO) and 164.027, 158.687, 144.789, 130.851, 129.086, 119.227, 117.115, 114.153, 66.153, 66.986, 42.741, 27.960. Mass spectrum M+ m/z 324.

EXAMPLE 32

5,7-Dibromo-4-methyl-6(2-imino-2-imidazolidine)-3-oxo-3,4-dihydro-(2H)-1,4-benzoxazine, hydrobromide.

The title compound is prepared by treating a solution of 4-methyl-6-(2-imino-2-imidazolidine)-3-oxo-3,4-dihydro-(2H)-1,4-benzoxazine in acetic acid with bromine and a catalytic amount of $H_2SO_4$ using the method illustrated in Example 5.

EXAMPLE 33

5-Bromo-4-methyl-6-(2-imino-2-imidazolidine)-3-oxo-3,4-dihydro-(2 H)-1,4-benzoxazine.

The title compound is prepared by debromination of 5,7-dibromo-4-methyl-6-(2-imino-2-imidazolidine)-3-oxo-3,4-dihydro-( 2H)-1,4-benzoxazine using the procedure illustrated in Example 15.

EXAMPLE 34

7-Bromo-4-methyl-6(2-imino-2-imidazolidine)-3,4-dihydro-(2H)-1,4-benzoxazine.

The title compound is prepared by LiAlH$_4$ mediated reduction of 7-bromo-4-methyl-6-(2-imino-2-imidazolidine)-3-oxo-3,4-dihydro-(2H)-1,4-benzoxazine in tetrahydrofuran using the procedure illustrated in Example 7.

EXAMPLE 35

5,7-Dibromo-4-methyl-6-(2-imino-2-imidazolidine)-3,4-dihydro-(2H)-1,4-benzoxazine.

The title compound is prepared by LiAlH$_4$ mediated reduction of 5,7-dibromo-4-methyl-6-(2-imino-2-imidazolidine)-3-oxo-3,4-dihydro-(2H)-1,4-benzoxazine in tetrahydrofuran using the procedure illustrated in Example 7.

EXAMPLE 36

5-Bromo-4-methyl-6-(2-imino-2-imidazolidine)-3,4-dihydro-(2H)-1,4-benzoxazine.

The title compound is prepared by LiAlH$_4$ mediated reduction of 5-bromo-4-methyl-6-(2-imino-2-imidazolidine)-3-oxo-3,4-dihydro-(2H)-1,4-benzoxazine in tetrahydrofuran using the procedure illustrated in Example 7.

EXAMPLE 37

7-methyl-6-nitro-3-oxo-3,4-dihydro-(2H)-1,4-benzoxazine and
5-methyl-6-nitro-3-oxo-3,4-dihydro-(2H)-1,4-benzoxazine.

Procedure: 6-nitro-3-oxo-3,4-dihydro-(2H)-1,4-benzoxazine (5 g, 25.7 mmol) was dissolved in 250 ml of anhydrous THF and cooled to 0 degrees C. CH$_3$MgBr (21 ml, 64.2 mmol) was added dropwise with vigorous stirring. After the final addition, the reaction was stirred for 15 min at 0 degrees C. A solution of KMnO$_4$ (2.7 g, 17.2 mmol) in acetone; H$_2$O (1:1) was prepared and cooled to 0 degrees C. The reaction mixture was poured into the KMnO$_4$ solution. The mixture was stirred for 15 min at 0 degrees C, then warmed to room temperature and stirred for another 15 min. The mixture was filtered through celite. The celite was then washed with EtoAC. The reaction was extracted with EtoAC. The combined organic layers were dried over MgSO$_4$ and evaporated leaving a bright yellow solid. The product was purified using flush chromatography (SiO$_2$, EtoAC: Hex, 3:7). Isolated 2.4 g (44.8%) of product which comprised a mixture of the title compounds which were not separated at this step.

EXAMPLE 38

6-Amino-5-methyl-3-oxo-3,4-dihydro-(2H)-1,4-benzoxazine and
6-Amino-7-methyl-3-oxo-3,4-dihydro-(2H)-1,4-benzoxazine.

A mixture of 5-methyl-6-nitro-3-oxo-3,4-dihydro-(2H)-1,4-benzoxazine and 7-methyl-6-nitro-3-oxo-3,4-dihydro-(2H)-1,4-benzoxazine (423 mg, 2.03 mmol) was dissolved in 25 ml of MeOH. The reaction was purged with argon gas, 10% Pd/C (21 mg, 5% w/w) was added and the mixture was hydrogenated for 16 hours at 40 PSI. The reaction mixture was filtered through celite and concentrated in vacuo. The residue was recrystallized from 3:1 CHCl$_3$: Hexane to yield 324 mg (89.7%) of the title compounds. The title compounds are separated by flash chromatography (SiO$_2$; 7:3 Hexanes:EtoAC). 'H NMR (DMSO) 5-methyl compound: and 10.41 (br, s 1H); 6.59 (d, 1H), 6.11 (d, 1H); 4.80 (br, 2H); 4.32 (s, 2H); 1.91 (s, 3H); 7-methyl compound: and 10.38 (brs, 1H); 6.52 (s, 1H); 6.18 (s, 1H); 4.57 (s, 2H); 4.32 (s, 2H); 1.92 (s, 3H); $^{13}$CNMR (DMSO) and 165.95, 142.08, 134.45, 125.67, 117.61, 116.03, 101.77, 67.16, 16.81.

EXAMPLE 39

7-methyl-6(2-imino-2-imidazolidine)-3-oxo-3,4-dihydro-(2H)-1,4-benzoxazine

Procedure: 7-methyl-6-amino-3-oxo-3,4-dihydro-(2H)-1,4-benzoxazine (150 mg, 0.842 mmol) and 2-imidazoline sulfonic acid (245 mg, 165 mmol) were suspended in 5 ml i-BuOH and heated to 125 degrees for 16 hours. The solvent was evaporated leaving a yellow oil. The product was purified by flash chromatography (SiO$_2$, CHCl$_3$: NH$_3$ Sat. MeOH, 4:6) collected 123.6 mg (59.6%) of a white solid. m.p. 225–230 decomp.; 'H NMR (DMSO, 300 MHz) and 6.697 (s, 1H), 6.446 (s, 1H), 4.421 (s, 2H), 3.250 (S, 4H), 1.984 (s, 3H); $^{13}$CNMR (DMSO, 75 MHz) and 165.459, 157.515, 143.076, 137.842, 125.278, 125.206, 117.378, 110.225 67.012, 42.106, 17.3737; MS M+ observed at m/z 246; High Resolution Mass Spectrum calc'd for C₁₂H₁₄O₂N₄ 246.1117 found 246.1101.

EXAMPLE 40

5-Methyl-6-(2-imino-2-imidazolidine)-3-oxo-3,4-dihydro-(2H)-1,4-benzoxazine.

The title compound is prepared from 6-amino-5-methyl-3-oxo-3,4-dihydro-(2H)-1,4-benzoxazine and 2-imidazoline-2-sulfonic acid using the method described in Example 39.

EXAMPLE 41

5,7-Dimethyl-6-nitro-3-oxo-3,4-dihydro-(2H)-1,4-benzoxazine.

The title compound is synthesized from 5-methyl-6-nitro-3-oxo-3,4-dihydro-(2H)-1,4-benzoxazine or from 7-methyl-6-nitro-3-oxo-3,4-dihydro-(2H)-1,4-benzoxazine and methyl magnesium bromide using the method illustrated in Example 37.

EXAMPLE 42

6-Amino-5-7,-dimethyl-3-oxo-3,4-dihydro-(2H)-1,4-benzoxazine.

The title compound is synthesized from 5,7-dimethyl-6-nitro-3-oxo-3,4-dihydro-(2H)-1,4-benzoxazine using the method illustrated in Example 38.

EXAMPLE 43

5,7-Dimethyl-6-(2-imino-2-imidazolidine)-3-oxo-3,4-dihydro-(2H)-1,4-benzoxazine.

The title compound is synthesized from 6-amino-5,7-dimethyl-3-oxo-3,4-dihydro-(2H)-1,4-benzoxazine and 2-imidazoline-2-sulfonic acid using the method illustrated in Example 39.

EXAMPLE 44

7-Methyl-6-(-2-imino-2-imidazolidine)-3,4-dihydro-(2H)-1,4-benzoxazine.

Procedure: 7-methyl-6-(2-imino-imidazolidine)-3-oxo-3,4-dihydro-(2H)-1,4-benzoxazine (100 mg, 0.406 mmol) was dissolved in 10 ml of THF. LiAlH₄ (15 mg, 4 equivalent of hydride, 0.406 mmol) was added with stirring at room temperature. The reaction mixture was then heated to reflux for 16 hours, and thereafter was quenched with H₂O and extracted with EtOAc. Extracts were dried and evaporated leaving a tan solid. The product was purified by flash chromatography (SiO₂, CHCl₃: NH₃ sat. MeOH, 95.5). Collected 52.6 mg (42%) of an off-white solid. MP 200–210 (decomp; ¹H NMR (300 MHz, CDCl₃) and 6.573 (s, 1H), 6.228 (s, 1H), 4.195 (t, J=4.12 Hz, 2H), 3.461 (s, 4H), 3.362 (t, J=4.4 Hz, 2H), 2.051 (s, 3H); ¹³C NMR (75 MHz, CDCl₃) and 157.541, 147.207, 140.845, 139.877, 131.450, 121.925, 118.161, 110.540, 65.311, 42.570, 41.250, 17.117.

EXAMPLE 45

5-Methyl-6-(2-imino-2-imidazolidine)-3,4-dihydro-(2H)-1,4-benzoxazine.

The title compound is prepared from 5-methyl-6-(2-imino-2-imidazolidine)-3-oxo-3,4-dihydro-(2H)-1,4-benzoxazine using the method described in Example 7.

EXAMPLE 46

5,7-Dimethyl-6-(2-imino-2-imidazolidine)-3,4-dihydro-(2H)-1,4-benzoxazine.

The title compound is synthesized from 5,7-dimethyl-6-(2-imino-2-imidazolidine)-3-oxo-3,4-dihydro-(2H)-1,4-benzoxazine using the method illustrated in Example 7.

EXAMPLE 47

5-ethyl-6-nitro-3-oxo-3,4-dihydro-(2H)-1,4-benzoxazine and
7-ethyl-6-nitro-3-oxo-3,4-dihydro-(2H)-1,4-benzoxazine.

The title compounds were prepared as an inseparable mixture, using the method illustrated in Example 37 except that ethyl magnesium bromide was substituted or methyl magnesium bromide to yield 1.2 g (35.3%) of products as a solid. ¹H NMR (DMSO, 300 MHz) and 10.982 (s, 1H), 7.555 (s, 1H), 7.058 (s, 1H); 4.735 (s, 2H), 2.809 (q, J=7.3 2H) 1.166 (t, J=6.89, 3H).

EXAMPLE 48

6-Amino-5-ethyl-3-oxo-3,4-dihydro-(2H)-1,4-benzoxazine and
6-Amino-7-ethyl-3-oxo-3,4-dihydro-(2)H-1,4-benzoxazine.

The title compounds were synthesized from the mixture of 5-ethyl-6-nitro-3-oxo-3,4-dihydro-(2H)-1,4-benzoxazine and 7-ethyl-6-nitro-3-oxo-3,4-dihydro-(2H(-1,4-benzoxazine using the method illustrated in Example 38. 6-Amino-5-ethyl compound: ¹H NMR (300 MHz, DMSO) and 10.42 (br, s, 1H); 6.60 (d, 1H); 6.12 (m, 1H); 4.65 (br, s, 2H); 4.36 (s, 2H); 2.32 (q, 2H); 1.06 (s, 3H); 6-Amino-7-ethyl compound ¹H NMR (300 MHz, DMSO) and 10.41 (br, s, 1H); 6.53 (s, 1H); 6.21 (s, 1H); 4.63 (br, s, 2H); 4.35 (s, 2H); 2.32 (q; 2H); 1.06 (s, 3H); ¹³C NMR (75 MHz, DMSO) and 165.98, 141.44; 134.71; 125.58; 171.97; 115.74; 102.15; 67.17; 22.86; 13.18.

EXAMPLE 49

5-Ethyl-6-(2-imino-2-imidazolidine)-3-oxo-3,4-dihydro-(2H)-1,4-benzoxazine. The title compound is synthesized from 6-amino-5-ethyl-3-oxo-3,4-dihydro-(2H)-1,4-benzoxazine and 2-imidazoline-2-sulfonic acid using the method illustrated in Example 39.

EXAMPLE 50

7-Ethyl-6-(2-imino-2-imidazolidine)-3-oxo-3,4-dihydro-(2H)-1,4-benzoxazine. The title compound was synthesized from 6-amino-7-ethyl-3-oxo-3,4-dihydro-(2H)-1,4-benzoxazine and 2-imidazoline-2-sulfonic acid using the method illustrated in example 39. Yield (57%) of title compound as a white crystalline solid, mp 250–270 degrees C. (decomp); ¹H NMR (300 MHz, DMSO) δ 6.77 (s, 1H); 6.54 (s, 1H); 4.49 (s, 2H); 3.42 (s, 4H); 2.40 (q, 2H); 1.03 (t, 3H); ¹³C NMR (75 MHz, DMSO) δ 165.25; 158;70; 140.62; 135.24; 133.87; 125.62; 116.25; 112.80; 66.95; 42.34; 23.40; 14.54.

EXAMPLE 51

5,7-Diethyl-6-nitro-3-oxo-3,4-dihydro-2H-1,4-benzoxazine.

The title compound is synthesized from either 5-ethyl-6-nitro-3-oxo-3,4-dihydro-(2H)-1,4-benzoxazine or from 7-ethyl-6-nitro-3-oxo-3,4-dihydro-(2H)-1,4-benzoxazine and ethyl magnesium bromide, using the procedure illustrated in Example 37.

EXAMPLE 52

6-Amino-5,7-diethyl-3-oxo-3,4-dihydro-(2H)-1,4-benzoxazine.

The title compound is synthesized from 5,7-diethyl-6-nitro-3-oxo-3,4-dihydro-2H-1,4-benzoxazine using the procedure illustrated in Example 38.

EXAMPLE 53

5,7-Diethyl-6-(2-imino-2-imidazolidine)-3-oxo-3,4-dihydro-(2H)-1,4-benzoxazine.

The title compound is synthesized from 6-amino-5,7-diethyl-3-oxo-3,4-dihydro-(2H)-1,4-benzoxazine using the procedure illustrated in Example 39.

EXAMPLE 54

5-Propyl-6-nitro-3-oxo-3,4-dihydro-(2H)-1,4-benzoxazine and 7-propyl-6-nitro-3-oxo-3,4-dihydro-(2H)-1,4-benzoxazine. The title compounds were prepared from 6-nitro-3-oxo-3,4-dihydro-(2H)-1,4-benzoxazine using the method illustrated in Example 37. For the 5-propyl-6-nitro compound: $^1$H NMR (300 MHz, DMSO) δ 10.65 (br s, 1H); 7.54 (d, 1H); 7.00 (d, 1H); 4.80 (s, 2H); 2.78 (distorted t, 2H); 1.50 (m, 2H); 0.90 (t, 3H). For the 7-propyl-6-nitro compound: $^1$H NMR (300 MHz, DMSO) δ 10.95 (br, 1H); 7.55 (s, 1H); 7.00 (s, 1H); 4.70 (s, 2H); 2.78 (distorted t, 2H); 1.50 (m, 2H); 0.90 (t, 3H).

EXAMPLE 55

6-Amino-5-propyl-3-oxo-3,4-dihydro-(2H)-1,4-benxozazine and
6-Amino-7-propyl-3-oxo-3,4-dihydro-(2H)-1,4-benzoxazine.

The title compounds were prepared from the mixture of 5-propyl-6-nitro-3-oxo-3,4-dihydro-(2H)-1,4-benzoxazine and 7-propyl-6-nitro-3-oxo-3,4-dihydro-(2H)-1,4-benzoxazine using the method illustrated in example 38. The title compounds were separated by flash chromatography on silica gel by elution with hexanes: ethyl acetate. For the 6-amino-5-propyl compound: $^1$H NMR (300 MHz, DMSO) δ 9.98 (br, 1H); 6.51 (d, 1H); 6.20 (d, 1H); 4.54 (s, 2H), 4.28 (s, 2H); 2.45 (t, 2H); 1.32 (m, 2H); 0.88 (t, 3H). For the 6amino-7-propyl compound: $^1$H NMR (300 NHz, DMSO) δ 10.41 (br s, 1H); 6.50 (s, 1H); 6.19 (s, 1H); 4.59 (br s, 2H); 4.34 (s, 2H); 2.29 (t, 2H); 1.45 (m, 2H); 0.88 (t, 3H); $^{13}$C NMR (75 MHz, DMSO) δ 165.51; 141.25; 134.17; 125.34; 120.12, 116.46; 101.97; 67.05; 32.14; 21.67; 13.90.

EXAMPLE 56

5-Propyl-6-(2-imino-2-imidazolidine)-3-oxo-3,4-dihydro-(2H)-1,4-benzoxazine.

The title compound is prepared from 6-amino-5-propyl-3-oxo-3,4-dihydro-(2H)-1,4-benzoxazine and 2-imidazoline-2-sulfonic acid using the method illustrated in Example 39.

EXAMPLE 58

7-propyl-6-(2-imino-2-imidazolidine)-3-oxo-3,4-dihydro-(2H)-1,4-benzoxazine.

The title compound was prepared from 6-amino-7-propyl-3-oxo-3,4-dihydro-(2H)-1,4-benzoxazine and 2-imidazoline-2-sulfonic acid using the method illustrated in Example 39. Yield: collected 106.7 mg (53%) of product as a white solid; $^1$H NMR (300 MHz, DMSO) δ 6.619 (s, 1H), 6.375 (s, 1H), 4.398 (s, 2H), 3.333 (s, 2H), 3.238 (s, 4H) 2.333 (t, J=8.09 Hz, 2H), 1.417 (m, 2H), 0.833 (t, 7.33, 3H); $^{13}$C NMR (75 MHz, DMSO) δ 165.499, 157.446, 144.525, 137.405, 129.750, 125.123, 116.353, 109.998, 67.025, 41.955; 32.840, 22.806, 13.881; MS M+ found at m/z 274; HRMS calc'd for $C_{14}H_{18}N_4O_2$ 274.1430, found 274.1429

EXAMPLE 59

7-Propyl-6-(2-imino-2-imidazolidine)-3,4-dihydro-(2H)-1,4-benzoxazine.

The title compound was prepared by LiAlH$_4$ mediated reduction of 7-propyl-6-(2-imino-2-imidazolidine)-3-oxo-3,4-dihydro-1,4-benzoxazine using the method illustrated in Example 7 $^1$H NMR (300 MHz, CDCl$_3$) δ 6.56 (s, 1H); 6.24 (s, 1H); 5.01 (br, 3H); 4.17 (s, 2H); 3.45 (s, 4H); 2.35 (t, 2H); 1.48 (m, 2H); 0.88 (t, 3H); $^{13}$C NMR (75 MHz, CDCl$_3$) δ 158.36; 140.78; 137.56; 131.75; 127.36; 117.28; 111.43; 65.35; 42.67; 41.09; 32.88; 23.63; 14.08; Mass spectrum m/e M+260.

EXAMPLE 60

5,7-Dipropyl-6-nitro-3-oxo-3,4-dihydro-(2H)-1,4-benzoxazine.

The title compound is synthesized from either 5-propyl-6-nitro-3-oxo-3,4-dihydro-(2H)-1,4-benzoxazine or 7-propyl-6-nitro-3-oxo-3,4-dihydro-(2H)-1,4-benzoxazine and propyl magnesium bromide using the method illustrated in Example 37.

EXAMPLE 61

6-Amino-5,7-dipropyl-3-oxo-3,4-dihydro-(2H)-1,4-benzoxazine.

The title compound is prepared from 5,7-dipropyl-6-nitro-3-oxo-3,4-dihydro-(2H)-1,4-benzoxazine using the method illustrated in Example 38.

EXAMPLE 62

5,7-Dipropyl-6-(2-imino-2-imidazolidine)-3-oxo-3,4-dihydro-(2H)-1,4-benzoxazine.

The title compound is synthesized from 6-amino-5,7-dipropyl-3-oxo-3,4-dihydro-(2H)-1,4-benzoxazine and 2-imidazoline-2-sulfonic acid using the method illustrated in Example 39.

EXAMPLE 63

5,7-Dipropyl-6-(2-imino-2-imidazolidine)-3,4-dihydro-(2H)-1,4-benzoxazine.

The title compound is synthesized from 5,7-dipropyl-6-(2-imino-2-imidazolidine)-oxo-3,4-dihydro-(2H)-1,4-benzoxazine using the method illustrated in Example 44.

EXAMPLE 65

5-Allyl-6-nitro-3-oxo-3,4-dihydro-(2H)-1,4-benzoxazine and
7-allyl-6-nitro-3-oxo-3,4-dihydro-(2H)-1,4-benzoxazine.

The title compounds are prepared from 6-nitro-3-oxo-3,4-dihydro-(2H)-1,4-benzoxazine and allyl magnesium bromide using the method illustrated in Example 37.

EXAMPLE 66

5-Allyl-6-amino-3-oxo-3,4-dihydro-(2H)-1,4-benzoxazine and
7-allyl-6-amino-3-oxo-3,4-dihydro-(2H)-1,4-benzoxazine.

The title compounds are synthesized by reduction of the mixture of 5-allyl-6-nitro-3-oxo-3,4-dihydro-(2H)-1,4-benzoxazine and 7allyl-6-nitro-3-oxo-3,4-dihydro-(2H)-1,4-benzoxazine using the procedure of Mahood and Schaffner *Org. Synth. Col. Vol. II* 1943, p. 160. The title compounds are separated by flash chromatography.

EXAMPLE 67

5-Allyl-6-(2-imino-2-imidazolidine)-3-oxo-3,4-dihydro-(2H)-1,4-benzoxazine.

The title compound is prepared from 5-allyl-6-amino-3-oxo-3,4-dihydro-(2H)-1,4-benzoxazine and 2-imidazoline-2-sulfonic acid, using the method illustrated in Example 39.

EXAMPLE 68

5-allyl-6-(2-imino-2-imidazolidine)-3,4-dihydro-(2H)-1,4-benzoxazine.

The title compound is synthesized from 5-allyl-6-(2-imino-2-imidazolidine)-3-oxo-3,4-(2H)-1,4-benzoxazine using the method illustrated in Example 44.

EXAMPLE 69

7-Allyl-6-(2-imino-2-imidazolidine)-3-oxo-3,4-dihydro-(2H)-1,4-benzoxazine.

The title compound is synthesized from 7-allyl-6-amino-3-oxo-3,4-dihydro-(2H)-1,4-benzoxazine and 2-imidazolidine-2-sulfonic acid using the procedure illustrated in Example 39.

EXAMPLE 70

7-Allyl-6-(2-imino-2-imidazolidine)-3,4-dihydro-(2H)-1,4-benzoxazine.

The title compound is synthesized from 7-allyl-6-(2-imino-2-imidazolidine)-3-oxo-3,4-dihydro-(2H)-1,4-benzoxazine using the method illustrated in Example 44.

EXAMPLE 71

5-(2-propyl)-6-nitro-3-oxo-3,4-dihydro-(2H)-1,4-benzoxazine and
7-(2-propyl)-6-nitro-3-oxo-3,4-dihydro-(2H)-1,4-benzoxazine.

The title compounds are prepared from 6-nitro-3-oxo-3,4-dihydro-(2H)-1,4-benzoxazine and 2-propyl magnesium bromide using the method illustrated in Example 37. The isomers are not separated at this step.

EXAMPLE 72

6-Amino-5-(2-propyl)-3-oxo-3,4-dihydro-(2H)-1,4-benzoxazine and
6-Amino-7-(2-propyl)-3-oxo-3,4-dihydro-(2H)-1,4-benzoxazine.

The title compounds are prepared from the mixture of 5-(2-propyl)-3-oxo-3,4-dihydro-(2H)-1,4-benzoxazine and 7(2-propyl)-3-oxo-3,4-dihydro-(2H)-1,4-benzoxazine using the method illustrated in Example 38. The isomers are separated by flash chromatography.

EXAMPLE 73

5-[(2-propyl)-6-(2-imino-2-imidazolidine)]-3-oxo-3,4-dihydro-(2H)-1,4-benzoxazine.

The title compound is prepared from 6-amino-5-(2-propyl)-3-oxo-3,4-dihydro-(2H)-1,4-benzoxazine and 2-imidazoline-2-sulfonic acid, using the method illustrated in Example 39.

EXAMPLE 74

5-[(2-Propyl)-6-(2-imino-2-imidazolidine)]-3,4-dihydro-(2H)-1,4-benzoxazine.

The title compound is synthesized from 5-[(2-propyl)-6-(2-imino-2-imidazolidine)]-3-oxo-3,4-dihydro-(2H)-1,4-benzoxazine, using the method illustrated in Example 44.

EXAMPLE 75

7-[(2-Propyl)-6-(2-imino-2-imidazolidine)]-3-oxo-3,4-dihydro-(2H)-1,4-benzoxazine.

The title compound is prepared from 6-amino-7-(2-propyl)-3-oxo-3,4-dihydro-(2H)-1,4-benzoxazine and 2-imidazoline-2-sulfonic acid using the method illustrated in Example 39.

EXAMPLE 76

7-[(2-Propyl)-6-(2-imino-2-imidazolidine)]-3,4-dihydro-(2H)-1,4-benzoxazine.

The title compound is synthesized from 7-[(2-propyl)-6-(2-imino-2-imidazolidine)]-3-oxo-3,4-dihydro-(2H)-1,4-benzoxazine using the procedure illustrated in Example 44.

EXAMPLE 77

1 8-methyl-7-nitro-3-oxo-3,4-dihydro-(2H)-1,4-benzoxazine, and 2 6-methyl-7-nitro-3-oxo-3,4-dihydro-(2H)-1,4-benzoxazine Procedure: 7-nitro-3-oxo-3,4-dihydro-(2H)-1,4-benzoxazine (5 g 25.7 mmol) was dissolved in 200 ml anhydrous THF and cooled to 0 degrees C. $CH_3MgBr$ (21 ml, 64.2 mmol) was added dropwise with vigorous stirring. After the final addition, the reaction was stirred for 15 minutes at 0 degrees C. and thereafter warmed to room temperature. A solution of $KMnO_4$ (2.7 g, 17.2 mmol) acetone: in $H_2O$ (1:1) was prepared and cooled to 0 degrees C. The reaction mixture was poured into the $KMnO_4$ solution with vigorous stirring. The mixture was stirred at 0 degrees C. for 15 minutes then at room temperature for 15 minutes. The reaction mixture was filtered through celite. The celite was then washed with EtOAc, and the reaction mixture was extracted with EtOAc. The combined organic layers were dried over $MgSO_4$ and evaporated leaving a yellow solid. The product was purified using flash chromatography (SiO2, EtOAc: Hex, 3:7). Isolated 1.2 g (22%) of the product as a mixture of isomers, which were not separate from one another but were carried on to next step. 8-methyl-7-nitro compound: 'H NMR (300 MHz, DMSO) δ 11.22 (brs, 1H); 7.65 (d, 1H); 6.88 (d, 1H); 4.67 (s, 2H); 2,45 (s, 3H); 6-methyl-7-nitro compound: 'H NMR (300 MHz, DMSO) δ 11.18 (br s, 1H); 7.61 (S, 1H); 6.85 (s, 1H); 4.70 (s, 2H); 2.36 (s, 3H).

EXAMPLE 78

7-Amino-6-methyl-3-oxo-3,4-dihydro-(2H)-1,4-benzoxazine and
7-Amino-8-methyl-3-oxo-3,4-dihydro-(2H)-1,4-benzoxazine.

A mixture of 6-methyl-7-nitro-and 8-methyl-7-nitro-3-oxo-3,4-dihydro-(2H)-1,4-benzoxazines (1 g, 4.80 mmol) was dissolved in 25 ml of MeOH. The reaction was purged with argon gas. 0.10% Pd/C (100 mg, 10% w/w) was added and the reaction was hydrogenated for 16 hours at 40 PSI. The reaction mixture was filtered through celite and evaporated leaving a white solid.

For the 7-Amino-6-methyl compound: $^1$H NMR (300 MHz, DMSO) δ 10.23 (brs, 1H); 6.45 (s, 1H); 6.23 (s, 1H); 4.64 (brs, 2H); 4.37 (s, 2H);
1.94 (s, 3H). For the 7-Amino-8-methyl compound: $^1$H NMR (300 MHz, DMSO) δ 10.23 (brs, 1H); 6.45 (d, 1H); 6.21 (d, 1H); 4.66 (brs, 2H); 4.42 (s, 2H); 1.90 (s, 3H). The title compounds are separated using flash chromatography on silica gel by elution with hexanes: ethyl acetate.

EXAMPLE 79

6-Methyl-7-(2-imino-2-imidazolidine)-3,4-dihydro-(2H)-1,4-benzoxazine.

The title compound is synthesized from 6-methyl-7-(2-imino-2-imidazolidine)-3-oxo-3,4-dihydro-(2H)-1,4-benzoxazine using the method illustrated in Example 44.

EXAMPLE 80

6-Methyl-7-(2-imino-2-imidazolidine)-3,4-dihydro-(2H)-1,4-benzoxazine. The title compound is synthesized from 6-methyl-7-(2-imino-2-imidazolidine)-3-oxo-3,4-dihydro-(2H)-1,4-benzoxazine using the method illustrated in Example 44.

EXAMPLE 81

8-Methyl-7-(2-imino-2-imidazolidine)-3-oxo-3,4-dihydro-(2H)-1,4-benzoxazine.

The title compound is synthesized from 7-amino-8-methyl-3-oxo-3,4-dihydro-(2H)-1,4-benzoxazine and 2-imidazolidine-2-sulfonic acid using the procedure illustrated in Example 39.

EXAMPLE 82

8-Methyl-7-(2-imino-2-imidazolidine)-3,4-dihydro-(2H)-1,4-benzoxazine.

The title compound is synthesized from 8-methyl-7-(2-imino-2-imidazolidine)-3-oxo-3,4-dihydro-(2H)-1,4-benzoxazine using the method illustrated in Example 44.

Following the procedures outlined above the following compounds can also be synthesized

EXAMPLE 83

6-Ethyl-7-(2-imino-2-imidazolidine)-3-oxo-3,4-dihydro-(2H)-1,4-benzoxazine.

EXAMPLE 84

6-Ethyl-7-(2-imino-2-imidazolidine)-3,4-dihydro-(2H)-1,4-benzoxazine.

EXAMPLE 85

8-Ethyl-7-(2-imino-2-imidazolidine)-3-oxo-3,4-dihydro-(2H)-1,4-benzoxazine.

EXAMPLE 86

8-Ethyl-7-(2-imino-2-imidazolidine)-3,4-dihydro-(2H),-1,4-benzoxazine.

EXAMPLE 87

6-Propyl-7-(2-imino-2-imidazolidine-3-oxo-3,4-dihydro-(2H)-1,4-benzoxazine.

EXAMPLE 88

6-Propyl-7-(2-imino-2-imidazolidine)-3,4-dihydro-(2H)-1,4-benzoxazine.

EXAMPLE 89

8-Propyl-7-(2-imino-2-imidazolidine)-3-oxo-3,4-dihydro-(2H)-1,4-benzoxazine.

EXAMPLE 90

8-Propyl-7-(2-imino-2-imidazolidine)-3,4-dihydro-2H-1,4-benzoxazine.

EXAMPLE 91

6-[(2-propyl)-7-(2-imino-2-imidazolidine)]-3-oxo-3,4-dihydro-(2H)-1,4-benzoxazine.

EXAMPLE 92

6-[(2-Propyl)-7-(2-imino-2-imidazolidine)]-3,4-dihydro-(2H)-1,4-benzoxazine.

EXAMPLE 93

8-[(2-Propyl)-7-(2-imino-2-imidazolidine)]-3-oxo-3,4-dihydro-(2H)-1,4-benzoxazine.

EXAMPLE 94

8-[(-2-Propyl)-7-(2-imino-2-imidazolidine)]-3,4-dihydro-(2H)-1,4-benzoxazine.

EXAMPLE 95

6-Allyl-7-(2-imino-2-imidazolidine)-3-oxo-3,4-dihydro-(2H)-1,4-benzoxazine.

EXAMPLE 96

6-Allyl-7-(2-imino-2-imidazolidine)-3,4-dihydro-(2H)-1,4-benzoxazine.

EXAMPLE 97

8-Allyl-7-(2-imino-2-imidolidine)-3-oxo-3,4-dihydro-2H-1,4-benzoxazine.

EXAMPLE 98

8-Allyl-7(2-imino-2-imidazolidine)-3,4-dihydro-2H-1,4-benzoxazine.

EXAMPLE 99

Imidazoline-2-sulfonic acid

2-Imidazolidinethione (Aldrich, 66.3 g, 650 mmol), Na$_2$MoO$_4$(5 g, 227 mmol) and NaCl (15 g. 256 mmol) were added to 300 ml H$_2$O. Although some dissolution occurred, a solid residue remained in the liquid of the mixture. The mixture was cooled to −10° C. using an immersion cooler. 500 ml of a 30% (w/v) aqueous H$_2$O$_2$ solution was placed in a jacketed controlled drop rate addition funnel and cooled to 0° C. using an ice/H₂O bath. The aqueous H₂O₂ solution was added to the mixture at a rate of 60 drops/min. The mixture was stirred for 16 hours at $-10°$ C. During this time, the mixture changed from a white suspension to a dark blue solution to a light blue suspension. At the end of 16 hours, a solid was filtered from the suspension and dried in vacuo. NO further purification was needed. Yield: 57.8 g (a yield of 52.3%) of the title compound as a white solid mp 157°–159° C.; H NMR (300 MHz, DMSO d₆) δ 10.38 (br, 2H); 3.85 (s, 4H). solid was stable when stored in the dark at 0° C. for at least 6 months.

What is claimed is:

1. A compound of the formula

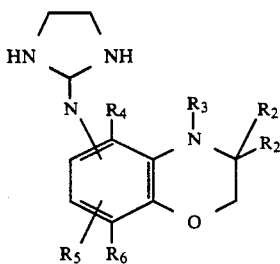

where:
R₂ is independently H, or lower alkyl of 1 to 6 carbons, or the two R₂ symbols jointly represent a carbonyl oxygen;
R₃ is H, lower alkyl of one to 6 carbons;
R₄ and R₅ independently is H, Br, lower alkyl of 1 to 6 carbons, or lower alkenyl with the proviso that when the R₂ groups symbolize a carbonyl oxygen or H then R₄ and R₅ both cannot be hydrogen;
R₆ is hydrogen, Br, or lower alkyl of 1 to 6 carbons, lower alkenyl, and
where the 2-imidazoline-2-yl)amino substituent is in the 6 position of the 1,4-benzoxazine nucleus.

2. A compound of the formula

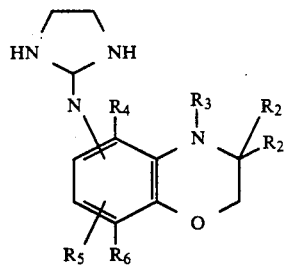

where:
R₂ is independently H, or lower alkyl of 1 to 6 carbons, or the two R₂ symbols jointly represent a carbonyl oxygen;
R₃ is H, lower alkyl of one to 6 carbons;
R₄ and R₅ independently is H, Br, lower alkyl of 1 to 6 carbons, or lower alkenyl with the proviso that when the R₂ groups symbolize a carbonyl oxygen or H then R₄ and R₅ both cannot be hydrogen;
R₆ is hydrogen, Br, or lower alkyl of 1 to 6 carbons, lower alkenyl, and
where the 2-imidazoline-2-yl)amino substituent is in the 7 position of the 1,4-benzoxazine nucleus.

3. A compound of the formula

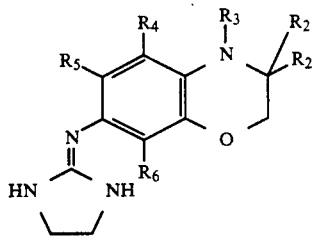

where:
R₂ is independently H, or lower alkyl of 1 to 6 carbons, or the two R₂ symbols jointly represent a carbonyl oxygen;
R₃ is methyl or hydrogen, both R₄ and R₅ are hydrogen, and R₆ is bromine, lower alkyl of 1 to 3 carbons or is allyl.

4. A compound of the formula:

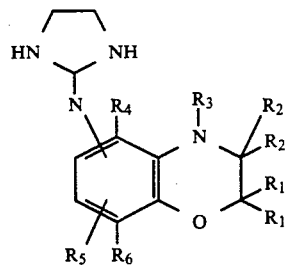

where
R₁ is independently H, or lower alkyl of 1 to 6 carbons;
R₂ is independently H, or lower alkyl of 1 to 6 carbons, or the two R₂ symbols jointly represent a carbonyl oxygen;
R₃ is H, lower alkyl of one to 6 carbons, O, OH and OR₇ where R₇ is lower alkyl of 1 to 6 carbons, or R₃ is COH or COR₈ where R₈ is lower alkyl of 1 to 6 carbons;
R₄ is H, bromine, lower alkyl or lower alkenyl;
R₅ is H, bromine, lower alkyl or lower alkenyl;
R₆ is H, bromine, lower alkyl or lower alkenyl, with the provisos that (i) at least one of the R₄, R₅ and R₆ groups is not hydrogen, (ii) when the R₂ groups symbolize a carbonyl oxygen or H then R₄ and R₅ both cannot be hydrogen, and (iii) the R₅ and the (2-imidazoline-2-yl)amino substituents are connected mutually exclusively to the 6 and 7 positions of the 1,4-benzoxazine nucleus.

5. A compound of the formula

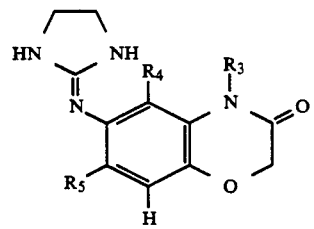

where:
R₃ is H, or methyl;

$R_4$ is selected from a group consisting of H, bromine, lower alkyl of 1 to 3 carbons, and allyl;

$R_5$ is selected from a group consisting of H, bromine, lower alkyl of 1 to 3 carbons, and allyl, with the proviso that both $R_4$ and $R_5$ cannot be hydrogen.

6. A compound of the formula

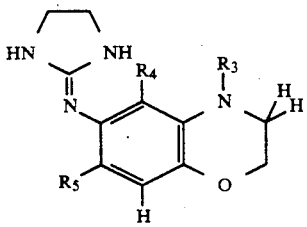

where:

$R_3$ is H, or methyl;

$R_4$ is selected from a group consisting of H, bromine, lower alkyl of 1 to 3 carbons, and allyl;

$R_5$ is selected from a group consisting of H, bromine, lower alkyl of 1 to 3 carbons, and allyl, with the proviso that both $R_4$ and $R_5$ cannot be hydrogen.

7. A compound of the formula

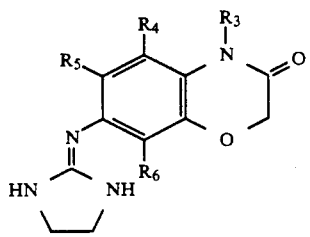

where:

$R_3$ is H, or methyl;

$R_4$ is selected from a group consisting of H, bromine, lower alkyl of 1 to 3 carbons, and allyl;

$R_5$ is selected from a group consisting of H, bromine, lower alkyl of 1 to 3 carbons, and allyl, with the proviso that both $R_4$ and $R_5$ cannot be hydrogen.

8. A compound of the formula

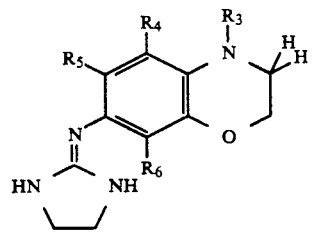

where:

$R_3$ is H, or methyl;

$R_4$ is selected from a group consisting of H, bromine, lower alkyl of 1 to 3 carbons, and allyl;

$R_5$ is selected from a group consisting of H, bromine, lower alkyl of 1 to 3 carbons, and allyl, with the proviso that both $R_4$ and $R_5$ cannot be hydrogen.

9. A compound of claim 4 where $R_4$ is bromine, lower alkyl or lower alkenyl.

10. A compound of claim 4 where $R_5$ is bromine, lower alkyl or lower alkenyl.

11. A compound of claim 4 where $R_6$ is bromine, lower alkyl or lower alkenyl.

12. A compound of claim 5 where one of $R_4$ and $R_5$ is hydrogen the other is bromine.

13. A compound of claim 5 where both $R_4$ and $R_5$ are bromine.

14. A compound of claim 5 where one of $R_4$ and $R_5$ is hydrogen and the other is lower alkyl of 1 to 3 carbons.

15. A compound of claim 5 where both $R_4$ and $R_5$ are lower alkyl of 1 to 3 carbons.

16. A compound of claim 5 where one of $R_4$ and $R_5$ is hydrogen and the other is an allyl group.

17. A compound of claim 6 where one of $R_4$ and $R_5$ is hydrogen the other is bromine.

18. A compound of claim 6 where both $R_4$ and $R_5$ are bromine.

19. A compound of claim 6 where one of $R_4$ and $R_5$ is hydrogen and the other is lower alkyl of 1 to 3 carbons.

20. A compound of claim 6 where both $R_4$ and $R_5$ are lower alkyl of 1 to 3 carbons.

21. A compound of claim 6 where one of $R_4$ and $R_5$ is hydrogen and the other is an allyl group.

22. A compound of claim 7 where one of $R_4$ and $R_5$ is hydrogen the other is bromine.

23. A compound of claim 7 where both $R_4$ and $R_5$ are bromine.

24. A compound of claim 7 where one of $R_4$ and $R_5$ is hydrogen and the other is lower alkyl of 1 to 3 carbons.

25. A compound of claim 7 where both $R_4$ and $R_5$ are lower alkyl of 1 to 3 carbons.

26. A compound of claim 7 where one of $R_4$ and $R_5$ is hydrogen and the other is an allyl group.

27. A compound of claim 8 where one of $R_4$ and $R_5$ is hydrogen the other is bromine.

28. A compound of claim 8 where both $R_4$ and $R_5$ are bromine.

29. A compound of claim 8 where one of $R_4$ and $R_5$ is hydrogen and the other is lower alkyl of 1 to 3 carbons.

30. A compound of claim 8 where both $R_4$ and $R_5$ are lower alkyl of 1 to 3 carbons.

31. A compound of claim 8 where one of $R_4$ and $R_5$ is hydrogen and the other is an allyl group.

* * * * *

UNITED STATES PATENT AND TRADEMARK OFFICE
CERTIFICATE OF CORRECTION

PATENT NO. : 5,091,528
DATED : February 25, 1992
INVENTOR(S) : Charles Gluchowski It is certified that error appears in the above-identified patent and that said Letters Patent is hereby corrected as shown below:

Column 1, line 44, ..."imidazlidine"... should be ...—imidazolidine—...;

Column 1, line 45, ..."benzoxazi" should be ...—benzoxazine—;

Column 3, line 57, the numeral "5" indicated on the bottom of the Formula 2 should be —8—;

Column 3, line 67, "N-substituent" should be —$\underline{N}$-substituent—;

Column 4, line 7, "n-propyl," should be —$\underline{n}$-propyl,—;

Column 4, line 47, "to" should be —and—;

Column 8, line 10, "the" should be —The—;

Column 9, line 8, "reaction" should be —reacting—;

Column 14, line 35, the "NH" on the left side of the structure should be —HN—;

Column 14, line 45, "(2 H)" should be —(2H)—;

Column 15, line 20, the double bond "O" is missing from structure 13; it should be attached to the carbon on the lower right of "NH";

Column 16, line 35, the "O" in the ring is missing from structure 15;

Column 18, line 65, "-C" should be —$^{13}$C—;

Column 19, line 55, "310.005:" should be —310.0055—;

Column 20, line 8, "6.8-dibromo-7"... should be —6,8-dibromo-7—...;

Column 20, line 52, ..."imidazlidine)"... should be ...—imidazolidine)—...;

Column 26, line 14, the ";" after "acetone" should be —:—;

Column 26, line 23, "flush" should be —flash—;

Column 26, line 41, "Hexane" should be —Hexanes—;

Column 28, line 18, "or" should be —for—;

Column 29, line 47, "6amino-7-propyl" should be —6-amino-7-propyl—;

UNITED STATES PATENT AND TRADEMARK OFFICE
CERTIFICATE OF CORRECTION

PATENT NO. : 5,091,528

DATED : February 25, 1992

INVENTOR(S) : Charles Gluchowski

It is certified that error appears in the above-identified patent and that said Letters Patent is hereby corrected as shown below:

Column 29, line 48, "NHz," should be —MHz,—;

Column 31, line 9, "7allyl"... should be —7-allyl—...;

Column 33, lines 29-32, delete "6-methyl-7-(2-imino-2-imidazolidine)-3-oxo, 3,4-dihydro-(2H)-1,4-benzoxazine using the method illustrated in Example 44." and insert in its place —7-amino-6-methyl-3-oxo-3,4-dihydro-(2H)-1,4-benzoxazine and 2-imidazoline-2-sulfonic acid using the method illustrated in Example 39.—;

Column 37, line 34, Claim 7, the "$R_6$" in the formula should be deleted; and

Column 37, line 54, Claim 8, the "$R_6$" in the formula should be deleted.

Signed and Sealed this

Twenty-first Day of December, 1993

BRUCE LEHMAN

*Attest:*

*Attesting Officer*  *Commissioner of Patents and Trademarks*

UNITED STATES PATENT AND TRADEMARK OFFICE
CERTIFICATE OF CORRECTION

PATENT NO. : 5,091,528

DATED : February 25, 1992

INVENTOR(S) : Charles Gluchowski

It is certified that error appears in the above-identified patent and that said Letters Patent is hereby corrected as shown below:

In Abstract, the formula, the bond connecting "N" with the upper ring should be double one;

Column 12, Scheme 3, between Compound 20 and Compound 21, the bond linking to "N" should be a double one, while the the bond linking to "NH" should be a single one;

Column 14, Scheme 3, Compound 21, the bond linking the lower "N" to the lower ring should be a double one;

Column 13, Scheme 3, Compound 24, "BR" should be --Br--;

Column 13, Scheme 3, Compound 25, "BR" should be --Br--;

Column 35, claim 1, in the formula, the bond linking the upper "N" to the upper ring should be a double one;

Column 35, claim 2, in the formula, the bond linking the upper "N" to the upper ring should be a double one;

UNITED STATES PATENT AND TRADEMARK OFFICE
CERTIFICATE OF CORRECTION

PATENT NO. : 5,091,528
DATED : Feb. 25, 1992
INVENTOR(S) : Charles Gluchowski

It is certified that error appears in the above-indentified patent and that said Letters Patent is hereby corrected as shown below:

Column 36, claim 4, in the formula, the bond linking the upper "N" to the upper ring should be a double one.

Signed and Sealed this

Fifth Day of July, 1994

Attest:

BRUCE LEHMAN

Attesting Officer    Commissioner of Patents and Trademarks